United States Patent [19]

Aranda et al.

[11] Patent Number: 5,322,844

[45] Date of Patent: Jun. 21, 1994

[54] ALKOXY-4 (1H)-PYRIDONE DERIVATIVES, PROCESSES FOR THE PREPARATION THEREOF, AND PHARMACEUTICAL COMPOSITIONS CONTAINING THEM

[75] Inventors: Julian Aranda, Vörstetten; Johannes Hartenstein, Stegen-Wittental; Reinhard Reck, Sexau; Christoph Schächtele, Freiburg; Claus Rudolph, Vörstetten; Hartmut Osswald, Emmendingen; Günter Weinheimer, Denzlingen, all of Fed. Rep. of Germany

[73] Assignee: Gödecke Aktiengesellschaft, Berlin, Fed. Rep. of Germany

[21] Appl. No.: 957,937

[22] Filed: Oct. 7, 1992

Related U.S. Application Data

[62] Division of Ser. No. 640,407, Jan. 28, 1991, Pat. No. 5,185,352.

[30] Foreign Application Priority Data

Aug. 6, 1988 [DE] Fed. Rep. of Germany ....... 3826846

[51] Int. Cl.$^5$ ................ A61K 31/535; A61K 31/495; A61K 31/445; C07D 401/06
[52] U.S. Cl. .................................. 514/235.5; 514/252; 514/318; 544/131; 544/295; 544/360; 546/193; 546/194
[58] Field of Search .................. 544/131, 295, 360; 546/193, 194; 514/235.5, 252, 318

[56] References Cited

U.S. PATENT DOCUMENTS 2,965,641  12/1960  Krimmel .......................... 544/131

FOREIGN PATENT DOCUMENTS 554715   3/1958  Canada .
978958  12/1975  Canada .
0120670  3/1984  European Pat. Off. .
3826846  2/1990  Fed. Rep. of Germany .
110674   6/1984  Japan .
110675   6/1984  Japan .

OTHER PUBLICATIONS

Imafuru et al. Bulletin of the Chemical Society of Japan, vol. 52, No. 1, 1979, pp. 107-110.
Looker et al., Journal of Heterocyclic Chemistry, vol. 23, No. 5, 1986, pp. 5-8.

Primary Examiner—Emily Bernhardt
Attorney, Agent, or Firm—Elizabeth M. Anderson

[57] ABSTRACT

The invention concerns new derivatives of certain alkoxy-4(1H)-pyridones, processes for preparing them, and pharmaceutical compositions containing them. The compounds of the invention are useful in the prevention and/or treatment of heart and blood vessel diseases such as thromboses, arteriosclerosis and hypertension, and of inflammatory processes, allergies, cancers, and certain degenerative damage of the central nervous system.

6 Claims, No Drawings

ALKOXY-4 (1H)-PYRIDONE DERIVATIVES, PROCESSES FOR THE PREPARATION THEREOF, AND PHARMACEUTICAL COMPOSITIONS CONTAINING THEM

CROSS REFERENCE TO RELATED APPLICATION

This is a division of U.S. application Ser. No. 07/640,407, filed Jan. 28, 1991, now U.S. Pat. No. 5,185,352.

BACKGROUND OF THE INVENTION

The compounds of formula I according to the present invention display useful pharmacological properties. In particular, they inhibit protein kinase C, a calcium- and phospholipid-dependent key enzyme, which plays a decisive part in the intracellular signal chain transduction (Y. Nishizuka, Science, 233, 305–312/1986) and is closely linked with the regulation of contractile, secretory and proliferative processes.

SUMMARY OF THE INVENTION

The invention concerns compounds of formula

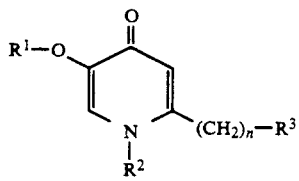

I and pharmaceutically acceptable salts thereof wherein $R^1$, $R^2$, $R^3$, and n are as described below.

The preferred compounds of the invention are those of formula I wherein
$R^1$ is a straight or branched, saturated or unsaturated alkyl of from 1 to 22 carbon atoms or adamantylalkyl containing from 1 to 22 carbon atoms;
$R^2$ is a straight or branched alkyl containing from 1 to 4 carbon atoms, cyclohexylmethyl, unsubstituted phenyl, phenylalkyl with from 1 to 5 carbon atoms in the straight or branched alkyl chain in which the phenyl ring is monosubstituted by halogen, hydroxyl, methyl, benzyloxy, methoxy or dimethylamino;
n is an integer of from 1 to 3; and
$R^3$ is selected from
a) halogen, hydroxyl, cyano, carboxamido alkoxycarbonyl of from 1 to 5 carbon atoms in the alkyl moiety or a radical of formula III, in which $R^6$ and $R^7$, which are each independently hydrogen, methyl, omegahydroxypropyl or benzyl;
b) a radical of formula IV, in which $R^8$ is hydrogen or methyl, $R^9$ and $R^{10}$ are each independently hydrogen, methyl, benzyl or phenylethyl and k is 2, 3 or 4;
c) formula V in which $R^{11}$ and $R^{12}$, are each independently hydrogen or methyl, X is an amino radical of formula VI, in which $R^{13}$ is hydrogen, phenyl, phenylalkyl or diphenylalkyl with from 1 to 5 carbon atoms in the straight or branched alkyl chain and where from 1 to 3 CH-groups in the phenyl ring are substituted by nitrogen or X is cyano or aminomethyl, and p and q are each 2; and
d) formula VIII, in which $R^9$ and $R^{10}$ are each methyl and r is 2 or 3.

More preferred compounds of the invention are those of formula I wherein
n is 1, 2 or 3;
$R^1$ is a decyl, tetradecyl, eicosanyl, octadecenyl, octadecyl, 2-octyldecyl or adamantylethyl;
$R^2$ is a propyl, methyl, phenyl, benzyl, methylbenzyl, chlorobenzyl, methoxybenzyl, cyclohexylmethyl, dimethylaminobenzyl, dimethylaminopropyl, benzyloxybenzyl, benzyloxyphenyl, phenylethyl, hydroxybenzyl or hydroxyphenyl; and
$R^3$ is bromine, hydroxy, cyano, amino, carboxamide, methoxycarbonyl, dimethylaminopropylamino, dimethylaminopropyl-N-methylamino, hydroxypropylamino, dimethylamino-N-methylamino, aminopropylamino, aminoethylamino, aminobutylamino, dimethylamino, dimethylaminopropoxy, N-benzyl-N-methylaminopropylamino, N-benzyl-N-methylamino, methoxycarbonylmethylpiperazino, benzylpiperazino, diphenylmethylpiperazino, aminomethylphenylpiperidino, phenylpiperazino, phenylethylpiperazino, pyrimidinylpiperazino or methylpiperazino.

Useful intermediates for preparing compounds of the instant invention include:
2-hydroxymethyl-5-octadecyloxy-4-pyranone,
2-hydroxymethyl-5-tetradecyloxy-4-pyranone,
5-eicosanyloxy-2-hydroxymethyl 4-pyranone,
5-butyloxy-2-hydroxymethyl-4-pyranone,
5-decyloxy-2-hydroxymethyl-4-pyranone,
2-hydroxymethyl-5-(9-cis-octadecenyloxy)-4-pyranone,
2 hydroxymethyl-5 (2-octyldecyloxy)-4-pyranone, 5-[2-(1-adamantyl)ethoxy]-2-hydroxymethyl-4-pyranone,
Still more preferred compounds of the instant invention are:
1-benzyl-2-hydroxymethyl-5-octadecyloxy-4(1H)-pyridone,
1-benzyl-5-butoxy-2-hydroxymethyl-4(1H)-pyridone,
1-benzyl-5-decyloxy 2-hydroxymethyl-4(1H)-pyridone,
1-benzyl-2-hydroxymethyl-5-tetradecyloxy-4(1H)-pyridone,
1-benzyl-5-eicoanyloxy-2-hydroxymethyl-4(1H)-pyridone,
1-benzyl-2-hydroxymethyl-5-(9-cisoctadecenyloxy)-4(1H) pyridone,
2-hydroxymethyl-1-(4-methylbenzyl)-5-octadecyloxy-4(1H)-pyridone,
1-(4-chlorobenzyl)-2-hydroxymethyl-5-octadecyloxy-4(1H) pyridone,
2-hydroxymethyl-1 (4-methoxybenzyl)-5-octadecyloxy-4(1H)-pyridone,
2-hydroxymethyl-1-(2-methoxybenzyl)-5-octadecyloxy-4(1H)-pyridone,
1-cyclohexylmethyl-2-hydroxymethyl-5-octadecyloxy-4(1H)-pyridone,
1-(4-dimethylaminobenzyl) 2-hydroxymethyl-5-octadecyloxy-4(1H)-pyridone,
1-(3-dimethylamonopropyl)-2-hydroxymethyl-5-octadecyloxy-4(1H)-pyridone,
1-(4-benzyloxyphenyl)-2-hydroxymethyl 5-octadecyloxy-4(1H)-pyridone,
1-benzyl-2-hydroxymethyl 5-(2-octyldecyloxy-4(1H)-pyridone,
5-[2-(1-adamantyl)ethoxy]-1-benzyl-2-hydroxymethyl-4(1H) pyridone,
(±)-2-hydroxymethyl-5-octadecyloxy-1-(1-phenylethyl)-4(1H)-pyridone,
(−)-2-hydroxymethyl-5-octadecyloxy-1 (1-phenylethyl)-4(1H)-pyridone, (+)-2-hydroxymethyl-5-octadecyloxy-1 (1-phenylethyl)-4(1H)-pyridone,
2-hydroxymethyl-5-octadecyloxy-1-propyl-4(1H)-pyridone,
2-hydroxymethyl-1-methyl-5-octadecyloxy-4(1H)-pyridone,
2-hydroxymethyl-5-octadecyloxy-1-phenyl-4(1H)-pyridone,
1-(4-benzyloxyphenyl) 2-hydroxymethyl-5-octadecyloxy-4(1H)-pyridone,
1-benzyl-2 bromomethyl-5-octadecyloxy-4(1H)-pyridone hydrobromide,
1-benzyl-2-bromomethyl-5-butoxy-4(1H)pyridone hydrobromide,
1-benzyl-2-bromomethyl-5-decyloxy-4(1H)-pyridone hydrobromide,
1-benzyl-2-bromomethyl-5-tetradecyloxy-4(1H)-pyridone hydrobromide,
1-benzyl-2-bromomethyl 5 eicosanyloxy-4(1H)-pyridone hydrobromide,
1-benzyl-2-bromomethyl-5-(9-cis-octadecenyloxy)-4(1H)-pyridone hydrobromide,
2-bromomethyl-1-(4-methylbenzyl)-5-octadecyloxy-4(1H)-pyridone hydrobromide,
2-bromomethyl-1-(4-chlorobenzyl)-5-octadecyloxy-4(1H) pyridone hydrobromide,
2-bromomethyl-1-(4-methoxybenzyl)-5-octadecyloxy-4(1H)-pyridone hydrobromide,
2-bromomethyl-1-(2-methoxybenzyl)-5-octadecyloxy-4(1H) pyridone hydrobromide,
2-bromomethyl-1-cyclohexylmethyl-5-octadecyloxy-4(1H)-pyridone hydrobromide,
2-bromomethyl-1-(4-dimethylaminobenzyl)-5-octadecyloxy-4(1H)-pyridone hydrobromide,
2-bromomethyl 5 octadecyloxy-1-propyl-4(1H)-pyridone hydrobromide,
2-bromomethyl-1-methyl-5-octadecyloxy-4(1H)-pyridone hydrobromide,
2-bromomethyl-5-octadecyloxy-1-phenyl-4(1H)-pyridone hydrobromide,
1-(4-benzyloxyphenyl)-2-bromomethyl-5-octadecyloxy-4(1H)-pyridone hydrobromide,
1-(4-benzyloxyphenyl)-2-bromomethyl-5-octadecyloxy-4(1H) pyridone hydrobromide,
1-benzyl-2-bromomethyl-5-(2-octyldecyloxy) 4(1H)-pyridone.hydrobromide,
5-[2-(1-adamantyl)ethoxy]-1-benzyl-2-bromomethyl-4(1H)-pyridone.hydrobromide,
(±)-2-bromomethyl-5-octadecyloxy-1-(1-phenylethyl)-4(1H)-pyridone.hydrobromide,
(−)-2-bromomethyl-5-octadecyloxy-1-(1-phenylethyl)-4(1H)-pyridone.hydrobromide,
(+)-2-bromomethyl-5-octadecyloxy-1-(1-phenylethyl)-4(1H)-pyridone.hydrobromide,
1-benzyl-2-[N-(3-dimethylaminopropyl)aminomethyl]-5-octadecyloxy-4(1H)-pyridone dioxalate,
1-benzyl-2-[N-(3-hydroxypropyl)-aminomethyl]-5-octadecyloxy-4(1H)-pyridone,
2-[N-(3-dimethylaminopropyl)-aminomethyl]-1-methyl-5-octadecyloxy-4(1H)-pyridone trihydrochloride hemihydrate,
1-benzyl-2-[N-(2 dimethylaminoethyl)-N-methylaminomethyl]-5-octadecyloxy-4(1H)-pyridone trihydrochloride,
2-[N-(3-hydroxypropyl)aminomethyl]-1-methyl 5- octadecyloxy-4(1H)-pyridone,
2-[N-(3-dimethylaminopropyl)aminomethyl]-5-octadecyloxy-1-propyl 4(1H) pyridone dioxalat,
2-[N-(3-aminopropyl)-aminomethyl]-1-methyl-5-octadecyloxy-4(1H) pyridone trihydrochloride,
2-[N-(3-aminopropyl)-aminomethyl]-1-benzyl 5-octadecyloxy 4(1H)-pyridone trihydrochloride,
2-[N-(3-aminopropyl)aminomethyl]-1-propyl-5-octadecyloxy-4(1H)-pyridone trihydrochloride,
1-benzyl-5-butyloxy-2-[N-(3-dimethylaminopropyl)aminomethyl]-4(1H)-pyridone dioxalate ¾ hydrate,
1-benzyl-5-decyloxy-2-[N-(3-dimethylaminopropyl)aminomethyl]-4(1H)-pyridone dioxalate hemihydrate,
1-benzyl-2-[N-(3 dimethylaminopropyl)-aminomethyl]-5-tetradecyloxy-4(1H) pyridone dioxalate monohydrate,
1-benzyl-2-[N-(3 dimethylaminopropyl)-aminomethyl]-5-eicosanyloxy-4(1H) pyridone dioxalate monohydrate,
2-[N-(2-aminoethyl)aminomethyl]-1-benzyl-5-octadecyloxy-4(1H)-pyridone ¼ hydrate,
1-cyclohexylmethyl-2-[N-(3 dimethylaminopropyl)-aminomethyl]-5-octadecyloxy-4(1H) pyridone difumarate,
1-(4-chlorobenzyl)-2-[N-(3 dimethylaminopropyl)aminomethyl]-5-octadecyloxy 4(1H)-pyridone difumarate 1.25 hydrate,
2-[N-(3-dimethylaminopropyl)aminomethyl]-5-octadecyloxy-1-phenyl-4(1H)-pyridone; diisopropyl ether,
1-benzyl-2-[N-(3-N-benzyl-N-methylaminopropyl)-aminomethyl]-5-octadecyloxy 4(1H) pyridone difumarate,
2[N-(3-dimethylaminopropyl)aminomethyl]-1-(4-methoxybenzyl)-5-octadecyloxy-4(1H)-pyridone trihydrochloride monohydrate,
1 benzyl-2-dimethylaminomethyl-5-octadecyloxy-4(1H)-pyridone oxalate hemihydrate,
2 [N-(3-dimethylaminopropyl)aminomethyl]-1-(2-methoxybenzyl)-5-octadecyloxy-4(1H)-pyridone difumarate,
1-benzyl-2-(N-benzyl-N-methylaminomethyl)-5-octadecyloxy-4(1H) pyridone,
2-[N-(3 dimethylaminopropyl)aminomethyl]-1-(4-methylbenzyl)-5 octadecyloxy-4(1H)-pyridone trihydrochloride hemihydrate,
2-[N-(4-aminobutyl)aminomethyl]-1-benzyl-5-octadecyloxy-4(1H)-pyridone trihydrochloride,
1-benzyl-2 [N-(3-dimethylaminopropyl)-aminomethyl]-5-(9 cis octadecenyloxy)-4(1H)-pyridone.trihydrochloride ½ H₂O,
1-(4-benzyloxyphenyl)-2 [N-(3-dimethylaminopropyl)aminomethyl]-5-octadecyloxy-4(1H)-pyridone,
1-(4-benzyloxyphenyl)-2-[N-(3-dimethylaminopropyl)aminomethyl]-5-octadecyloxy-4(1H)-pyridone.difurmarate.2,5 H₂O,
1-benzyl-2 [N-(3 dimethylaminopropyl)-aminomethyl]-5-(2 octyldecyloxy)-4(1H)-pyridone.trihydrochloride.⅜H₂O,
5-(2-adamantylethoxy)-1-benzyl-2-[N-(3-dimethylaminopropyl)aminomethyl]-4(1H)-pyridone,
(±)-1 benzyl-5 octadecyloxy)-2-(N-[3-(1-phenylethyl)aminopropyl]aminomethyl)-4(1H)-pyridone.trihydrochloride,
2-[N-(3-dimethylaminopropyl)aminomethyl]-1-(4-hydroxybenzyl)-5-octadecyloxy-4(1H)-pyridone.dihydrochloride.2 H₂O,
2-[N-(3 dimethylaminopropyl)aminomethyl]-1-(4-hydroxyphenyl)-5-octadecyloxy-4(1H)-pyridone.trihydrochloride.0,5 H₂O, 1-[(1-benzyl-5 octadecyloxy-4(1H)-pyridon-2-yl)-methyl]-4-cyano 4 phenylpiperidine dihydrochloride,
1-[(1 benzyl-5 octadecyloxy-4(1H)-pyridon-2-yl)-methyl]-4-methoxycarbonyl-2-methyl-piperazine dihydrochloride ¾ hydrate,
1-[(1-benzyl-5-octadecyloxy-4(1H) pyridon-2-yl)-methyl]-4-benzylpiperazine,
1-benzyl-2 [N-(3 dimethylaminopropyl)-N-methylaminomethyl]-5-octadecyloxy-4(1H) pyridone trihydrochloride,
1-[(1-benzyl-5-octadecyloxy-4(1H) pyridon-2-yl)-methyl]-4-diphenylmethylpiperazine sesquioxalate monohydrate,
1-[(1-benzyl 5-octadecyloxy-4(1H) pyridone-2-yl)-methyl]-4-phenylpiperazine.dihydrochloride.H₂O,
1-[(1-benzyl 5-octadecyloxy-4(1H) pyridone-2 yl)-methyl]-4-(2-pyrimidinyl)piperazine,
1-[(1-benzyl-5-octadecyloxy-4(1H) pyridone-2-yl)-methyl]-4-benzylpiperazine.dioxalate.½H₂O,
1-[(1-benzyl 5-octadecyloxy-4(1H)-pyridone 2 yl)-methyl]-4-(2 phenylethyl)piperazine.trihydrochloride.½H₂O,
1-[(1-benzyl 5-decyloxy-4(1H)-pyridone-2-yl)-methyl]-4-(2-phenylethyl)piperazine.dihydrochloride,
1-[(1-benzyl-5-benzyloxy-4(1H)-pyridone-2-yl)-methyl]-4-benzylpiperazine.trihydrochloride,
(±)-1-[(1-benzyl-5-octadecyloxy-4(1H)-pyridone-2-yl)-methyl]-4-(1-phenylethyl)-piperazine.trihydrochloride ⅔H₂O,
(±)-1-[(5-octadecyloxy-1-(1-phenylethyl)-4(1H)-pyridone-2-yl)-methyl-4-benzylpiperazine,
(−)-1-[(5-octadecyloxy-1-(1-phenylethyl)-4(1H)-pyridone-2-yl)-methyl]-4-benzylpiperazine,
(+)-1-[(5-oOctadecyloxy-1-(1-phenylethyl)-4(1H)-pyridone-2-yl)-methyl]-4-benzylpiperazine,
1-[(1-bBenzyl-5-octadecyloxy-4(1H) pyridon-2 yl)-methyl]-4-aminomethyl-4-phenylpiperidine trihydrochloride,
(±)-1-[(1-benzyl-5-octadecyloxy-4(1H)-pyridon 2-yl)methyl]-2 methylpiperazine fumarate,
1-benzyl-2-(3-dimethylaminopropoxymethyl)-5-octadecyloxy-4(1H)-pyridone dihydrochloride,
2 (3-dimethylaminopropoxymethyl)-1-methyl-5-octadecyloxy 4(1H)-pyridone dihydrochloride,
2-(3-dimethylaminopropoxymethyl)-5-octadecyloxy-1-propyl-4(1H)-pyridone dihydrochloride ⅔hydrate,
2-(3-dimethylaminopropoxymethyl)-1-(4-methylbenzyl)-5-octadecyloxy-4(1H)-pyridone dihydrochloride sesquihydrate,
2-(3-dimethylaminopropoxymethyl)-1-(4-methoxybenzyl)-5-octadecyloxy-4(1H) pyridone dihydrochloride ⅓hydrate,
1-cyclohexylmethyl-2-(3-dimethylamino-propoxymethyl)-5-octadecyloxy-4(1H) pyridone oxalate,
1-(4-chlorobenzyl)-2-(3-dimethylamino-propoxymethyl)-5-octadecyloxy-4(1H) pyridone dihydrochloride 2.5 hydrate,
2-(3-dimethylaminopropoxymethyl) 1-(2-methoxybenzyl)-5-octadecyloxy-4(1H) pyridone sesquihydrate,
3-[1-benzyl-5-octadecyloxy-4(1H) pyridon-2-yl]-propionic acid nitrile hydrochloride,
3-[1-methyl-5-octadecyloxy-4(1H) pyridon-2-yl]-propionic acid nitrile,
3-[1-benzyl 5 octadecyloxy-4(1H) pyridon-2-yl]propylamine dihydrochloride,
methyl 3-[1-benzyl-5-octadecyloxy-4(1H)-pyridon-2-yl]-propionate,
3-[1-benzyl-5-octadecyloxy-4(1H) pyridon-2 yl]-propanol, and
3-[1-benzyl 5-octadecyloxy-4(1H) pyridon-2-yl]-propionic acid amide.

The invention also concerns pharmaceutical compositions for treating and/or preventing heart and/or blood vessel diseases which comprise a therapeutically effective amount of a compound of formula I in admixture with a pharmaceutically acceptable carrier.

The invention also concerns a method of treating and/or preventing heart and blood vessel diseases such as thromboses, arteriosclerosis, and hypertension and other diseases such as inflammatory processes, allergies, cancers, and certain degenerative damage to the central nervous system.

DESCRIPTION

The present invention is concerned with new alkoxy-4(1H)-pyridone derivatives, processes for the preparation thereof and pharmaceutical compositions containing them.

DETAILED DESCRIPTION OF THE INVENTION

The new alkoxy-4(1H)-pyridone derivatives of the present invention are compounds of formula

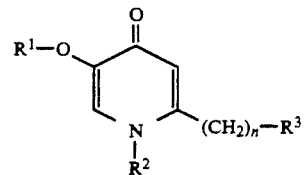

wherein $R^1$ is a straight-chained or branched, saturated or unsaturated alkyl or adamantylalkyl radical having up to 22 carbon atoms, $R^2$ is a straight-chained or branched, saturated or unsaturated alkyl radical having up to 5 carbon atoms, a cycloalkylmethyl radical having 5 to 7 carbon atoms in the cycloalkyl ring, an unsubstituted phenyl or phenylalkyl radical with up to 5 carbon atoms in the straight or branched alkyl chain or a phenyl or phenylalkyl radical with up to 5 carbon atoms in the straight or branched alkyl chain substituted by halogen, hydroxyl, alkyl containing up to 5 carbon atoms, alkoxyl having up to 5 carbon atoms, dialkylamino having up to 5 carbon atoms or benzyloxy or is an aminoalkyl radical of the formula

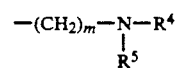

wherein $R^4$ and $R^5$, which are the same or different, are hydrogen atoms or alkyl radicals having 1 to 3 carbon atoms and m is a whole number of from 2 to 5, n is a whole number of from 1 to 5 and $R^3$ is either a) a halogen atom, a hydroxyl, cyano or carboxamido group or an alkoxycarbonyl radical having up to 5 carbon atoms in the alkyl moiety or an amino group of formula

wherein $R^6$ and $R^7$, which are the same or different, are hydrogen atoms, alkyl or omega-hydroxyalkyl radicals having up to 5 carbon atoms or phenyl or phenylalkyl radicals with up to 5 carbon atoms in the straight or branched alkyl chain which the phenyl ring is either unsubstituted or substituted by halogen, hydroxyl, alkyl having up to 5 carbon atoms, alkoxy having up to 5 carbon atoms, dialkylamino b) an amino radical of formula

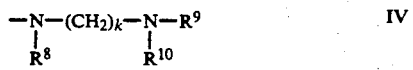   IV wherein $R^8$ is a hydrogen atom or an alkyl radical having up to 5 carbon atoms and $R^9$ and $R^{10}$, which are the same or different, are hydrogen atoms, alkyl radicals having up to 5 carbon atoms or phenyl or phenylalkyl with up to 5 carbon atoms in the straight or branched alkyl chain radicals which phenyl ring is either unsubstituted or substituted by halogen, hydroxyl, alkyl having up to 5 carbon atoms, alkoxy having up to 5 carbon atoms, dialkylamino having up to 5 carbon atoms or benzyloxy and k is a whole number of from 2 to 5; or c) a heterocycle of the formula

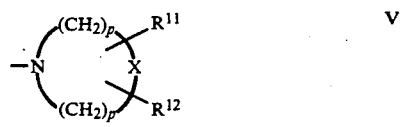   V wherein $R^{11}$ and $R^{12}$, which are the same or different, are hydrogen atoms, alkyl radicals having up to 3 carbon atoms or phenyl or phenylalkyl radicals with up to 5 carbon atoms in the straight or branched alkyl chain, X is an oxygen atom, an amino group of the formula

   VI wherein $R^{13}$ is a hydrogen atom or a phenyl, phenylakyl or diphenylalkayl with from 1 to 5 carbon atoms in the straight or branched alkyl chain and where in the phenyl ring up to three CH— groups may be substituted by nitrogen, or X is a radical of formula

   VII wherein $R^{14}$ is a hydrogen atom or a phenyl radical which is either unsubstituted or substituted by halogen, hydroxyl, alkyl containing up to 5 carbon atoms, alkoxy containing up to 5 carbon atoms, dialkylamino containing up to 5 carbon atoms or benzyloxy and $R_{15}$ is a hydrogen atom, a hydroxyl or cyano group or a hydroxymethyl, aminomethyl, carboxamide, ethoxy or methoxycarbonyl radical and p and q, which are the same or different, signify 2 or 3; or d) a radical of formula

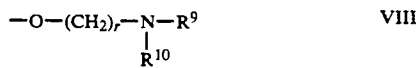   VIII wherein $R^9$ and $R_{10}$ have the above-given meanings and r is a whole number of from 2 to 5; and the pharmacologically acceptable salts thereof.

Preferred compounds of the present invention are those wherein $R^1$ is a straight-chained or branched, saturated or unsaturated alkyl radical containing 10 to 22 carbon atoms or an adamantylethyl radical, $R^2$ is a methyl, ethyl, propyl or a cyclohexylmethyl radical, a phenyl, benzyl or phenylethyl radical which is either unsubstituted or monosubstituted by halogen, hydroxyl, methyl, benzyloxy, methoxy or dimethylamino, or an aminoalkyl radical of the general formula II, wherein $R^4$ and $R^5$ is a methyl group and m is 2 to 4 and $R^3$.

a) if n is 1 is a radical of formula III in which $R^6$ and $R^7$, which are the same or different, are hydrogen atoms or methyl, omega-hydroxypropyl or benzyl radicals; or b) an amino radical of formula IV, in which $R^8$ is a hydrogen atom or a methyl radical, $R^9$ and $R^{10}$, which are the same or different, are hydrogen atoms or methyl, benzyl or phenylethyl radicals and k is 2, 3 or 4; or c) a heterocycle of formula V in which $R^{11}$ and $R^{12}$, which are the same or different, are hydrogen atoms or methyl radicals, X is an amino radical of general formula VI, in which $R^{13}$ is a hydrogen atom or a phenyl, benzyl, pyrimidinyl, diphenylmethyl or phenylethyl radical or X is a radical of formula VII, in which $R^{14}$ is a phenyl radical, $R^{15}$ is a cyano or aminomethyl radical and p and q are 2.

Especially preferred are compounds of formula I wherein $R^3$ is one of the following heterocyclic structures:

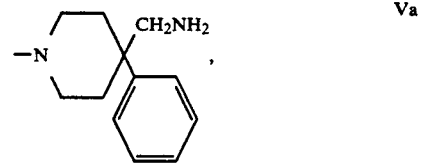   Va

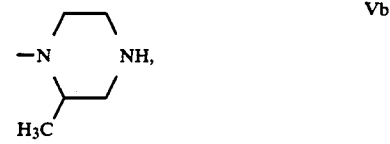   Vb

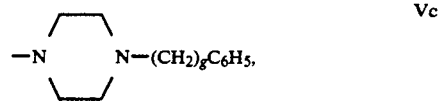   Vc

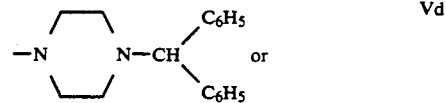   Vd

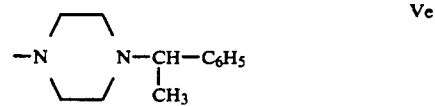   Ve where in Vc g has the meaning of 0, 1 or 2.

Also preferred are compounds of formula I in which, when n is 1, $R^3$ stands for a radical of formula VIII, in which $R^9$ and $R^{10}$ are methyl radicals and r is 2 or 3 or, when n is 2 or 3, $R^3$ is an amino, cyano, hydroxyl, methoxycarbonyl or carboxamide group.

The present invention also provides a process for the preparation of the new alkoxy 4(1H)-pyridone derivatives of general formula (I), wherein either a) a compound of the formula IX:

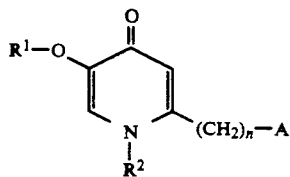

IX in which $R^1$ and $R^2$ have the above-given meanings, n is 1 and A is a nucleofugic group which can be split off, is reacted in known manner with an amino compound of the formula X, XI or XII:

X

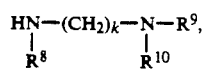

XI

XII in which $R^6$, $R^7$, $R^8$, $R^9$, $R^{10}$, $R^{11}$, $R^{12}$, k, p, q and X have the above-given meanings; or b) a compound of formula XIII:

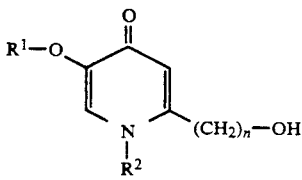

XIII in which $R^1$ and $R^2$ have the above-given meanings and n is 1, is reacted with a compound of formula XIV:

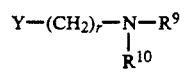

XIV in which $R^9$, $R^{10}$ and r have the above-given meanings and Y is a group which can be split off, in an appropriate solvent under basic conditions; or c) when n is 2 or 3 and $R^3$ is amino, hydroxyl, cyano, methoxycarbonyl or carboxamide, a 2-halo methylpyridone of formula IXa:

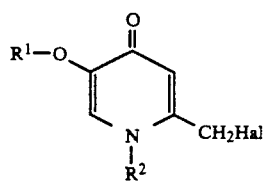

IXa in which $R^1$ and $R^2$ have the above-given meanings and Hal is a halogen atom, is reacted with a cyanoacetic acid ester in known manner, saponified and decarboxylated and from the cyano compound thus obtained of formula Ia:

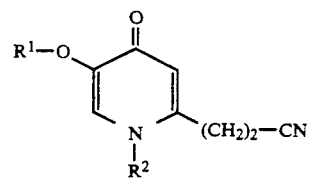

Ia in which $R^1$ and $R^2$ have the above-given meanings. An ester, amino, hydroxyl or amido compound of formula I is prepared according to methods known from the literature.

The following Scheme I illustrates this latter process.

SCHEME I

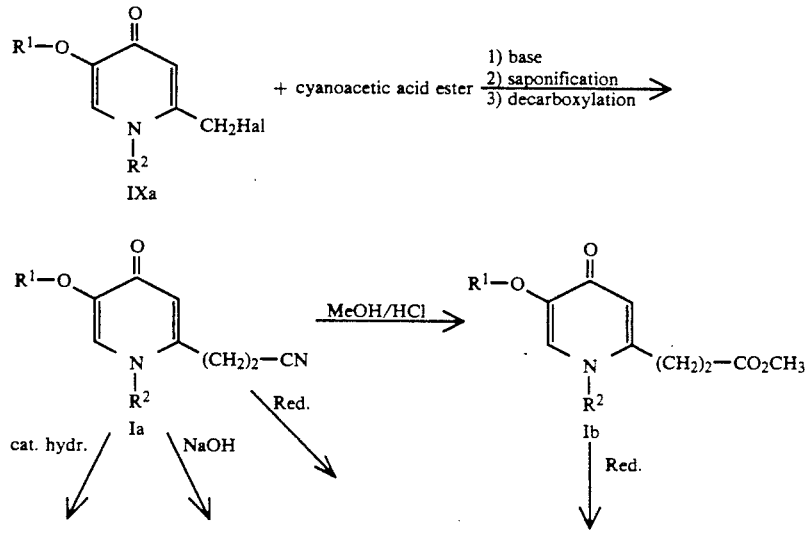

SCHEME I

-continued

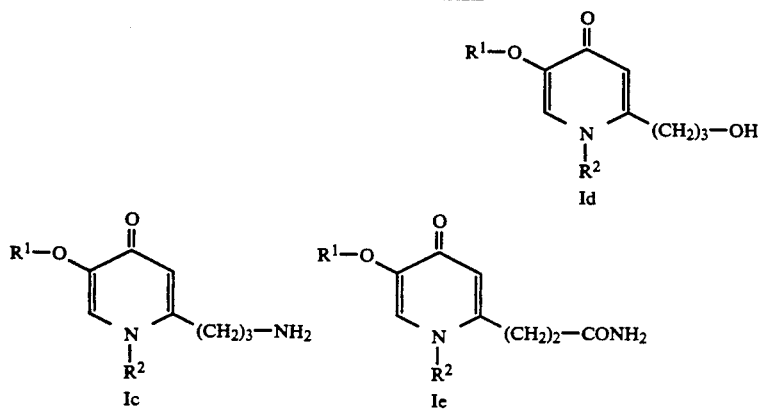

The reaction according to process a) is carried out in the presence of an inert solvent, such as methanol, ethanol, propanol or propan-2-ol and preferably in ethanol or propan-2-ol, at a temperature of from 20° to 90° C. and preferably of from 60° to 80° C. The group A which can be split off is preferably a halogen atom and especially a bromine atom.

In the case of an advantageous embodiment of the nucleophilic substitution of the residue A in (IX) by the amino compounds used of formula X, XI and XII, the reaction is carried out in the presence of a base as acid-binding agent, triethylamine or potassium carbonate preferably being used. It is possibly advantageous to use an excess of the amino derivative employed since it then simultaneously acts as acid-binding agent. The reaction time is from 1 to 8 hours and is usually from 2 to 3 hours. Purification of the product obtained is carried out in the usual manner, for example by recrystallization from a solvent, conversion into an acid-addition salt or column chromatography.

When $R^3$ in formula I is a heterocycle of the formula Va:

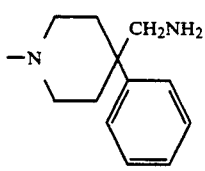

a compound of formula IX is first reacted with 4-cyano 4-phenylpiperidine (XIIa) and thereafter the cyano group is reduced to an aminomethyl radical with Raney nickel and hydrogen. The reaction is advantageously carried out in an autoclave with methanol saturated with ammonia at a temperature of from 40° to 100° C. and preferably of about 60° C. at a pressure of from 40 to 120 bar and preferably of about 60 bar.

When $R^3$ in formula I is a heterocycle of formula Vb:

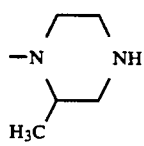

a compound of formula IX is reacted with a piperazine derivative of formula XIIb:

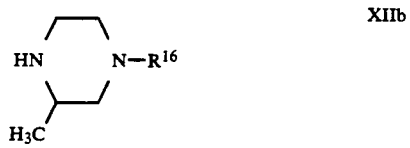

wherein $R^{16}$ is a protective group, for example an ethoxy, methoxy, tert.-butoxy or benzyloxycarbonyl radical and preferably a methoxycarbonyl radical and the protective group is subsequently split off. The splitting off of the protective group takes place according to conventional methods under acidic conditions. The splitting off of the protective group $R^{16}$ is preferably carried out with hydrogen bromide in glacial acetic acid in a closed vessel at normal pressure at a temperature of from 5° to 25° C. and preferably of about 20° C.

In the case of process variant b), the reaction is preferably carried out in a polar aprotic solvent, for example dimethylformamide or dimethyl sulphoxide, in the presence of an appropriate base, preferably sodium hydride (cf. European Patent Specification No. 0 171 814 which corresponds to U.S. Pat. Nos. 4,603,144, 4,735,964, and 4,812,474). The reaction is carried out at a temperature of from 20° to 100° C. and preferably of from 50° to 60° C. Purification of the product obtained again takes place by recrystallization from a solvent, conversion into an acid addition salt or column chromatography.

The removable group Y of the starting compound of formula XIV can be a halogen atom, preferably a chlorine or bromine atom and especially a chlorine atom. Furthermore, as removable groups there can, for example, also be used aromatic and aliphatic sulphonic acid residues, for example a p-toluenesulphonic acid or methanesulphonic acid radical.

In the case of process variant c), the compounds of formula Ia are prepared by reacting a 2-bromomethyl-pyridone derivative of formula IXa, wherein $R^1$ and $R^2$ have the above-given meanings, with tert.-butyl cyanoacetate. The reaction is advantageously carried out in an inert polar aprotic solvent, preferably in dimethylformamide, in the presence of a base, preferably of potassium tert.-butylate, at a temperature of from 20° to 100° C., and preferably of from 50 to 60° C.. The intermediate products thus obtained are subjected to an acidic or alkaline hydrolysis, an alkaline hydrolysis preferably being used, for example at ambient temperature in aqueous sodium or potassium hydroxide solution and methanol. The carboxylic acid group in the compound obtained is now split off by known methods, for example by melting or heating in a high boiling solvent.

By catalytic hydrogenation of the cyano group in the compounds of formula Ia, there are prepared the compounds of formula Ib. The reaction advantageously takes place in an autoclave with methanolic ammonia and Raney nickel as catalyst at a temperature of from 40° to 100° C. and preferably of about 60° C. and at a pressure of from 40 to 120 bar and preferably of about 60 bar.

When, in compounds of formula I, $R^3$ is a methoxycarbonyl radical and n is 2, the corresponding cyano compounds of formula Ia can be reacted with methanolic hydrogen chloride. The reaction is preferably carried out in a closed vessel at normal pressure and at ambient temperature with subsequent hydrolysis. By reaction of a compound of formula Ia with sodium borohydride in boiling propan-2-ol and subsequent treatment with sodium hydroxide solution, there are obtained alkoxy-4(1H)-pyridone derivatives of general formula (Id) and (Ie) (cf, R.A. Egli, Helv. Chim. Acta, 53, 47/1970).

The compounds of formula Ia–Ie can be purified, for example, by column chromatography, conversion into an acid and/or recrystallization from a solvent. If desired, the compounds of formula Ia can be converted into compounds of formula Ie in known manner by hydrolysis with aqueous or alcoholic alkali metal hydroxide solutions, for example potassium hydroxide or sodium hydroxide, at ambient temperature.

If desired, the compounds of formula Ib can be converted into compounds of formula Id by reduction of the carboxylic acid ester radical. The reduction can be carried out by generally known methods, for example with complex metal hydrides, such as sodium borohydride, in tert.-butanol/methanol (cf. K. Soai, Synthetic Communications, 12, 463/1982).

The 4(1H) pyridone derivatives of formulae IX and XIII used as intermediate products, wherein $R^1$ and $R^2$ have the above given meanings, n is 1 and A is a bromine atom, are prepared from kojic acid according to processes known from the literature, as shown by the following reaction Scheme II.

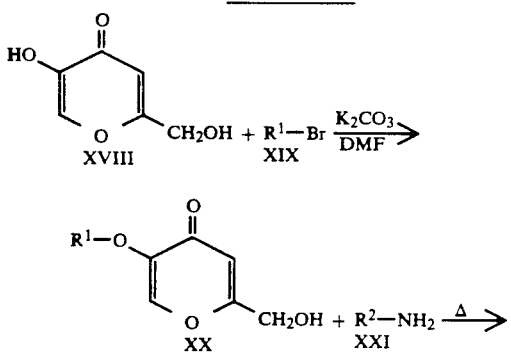

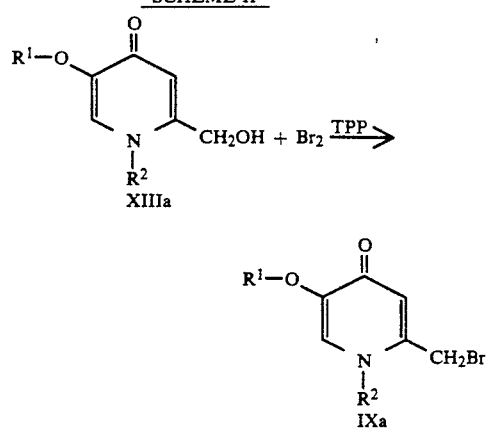

Kojic acid (XVIII) is thereby reacted with an appropriate alkyl bromide (XIX) according to the usual processes described in the literature (for example in U.S. Pat. No. 4,644,071; European Patent Specification No. 0 171 814; A. F. Thomas and A. Marxer, Helv. Chim. Acta, 43, 469/1960; and European Patent Specification No. 0 209 751 which corresponds to U.S. Pat. No. 4,758,557). This reaction is preferably carried out with potassium carbonate as base and dimethylformamide as solvent.

The 2-hydroxymethyl-4(1H)-pyridone derivatives of formula XIIIa are prepared by reacting in known manner (cf. for example, Counsell et al., J. Med. Chem., 17(1), 1–5/1974; J. H. Looker and M. D. Cliffton, J. Heterocyclic Chem., 23, 5/1986; Tsutomu Teitei, Austr. J. Chem., 36, 2307–2315/1983; Canadian Patent No. 978,958: S. Hünig and G. Köbrich, Liebigs Ann. Chem., 609, 181/1958: K. Imafuku et al., Bull. Chem. Soc. Japan, 52, 107/1979) a pyranone derivative of formula XX with an amine of formula XXI at a temperature of from 80 to 120° C. and preferably of about 100° C. In the case of amines with a low boiling point, the reaction is carried out in an autoclave in the presence of an inert polar solvent, for example ethanol. The products are purified by column chromatography or crystallization.

For the conversion of the hydroxymethyl radical in compounds of formula XIII into a bromoethyl radical, it is especially preferred to use triphenyl phosphine dibromide, prepared from bromine and triphenylphosphine (cf. Fieser and Fieser, Reagents for Organic Synthesis, pub. Wiley-Interscience, 1975, Vol. 5, p. 729). The reaction is carried out by reacting a solution or suspension of triphenylphosphine dibromide, prepared in situ, in an appropriate anhydrous solvent, preferably dichloromethane or toluene, with the 2-hydroxymethyl-4(1H)-pyridone compound of formula XIII in question at a temperature of from 30 to 100° C. and preferably at about 50° C. when using dichloromethane as solvent or at 70° C. when using toluene as solvent. The 2-bromomethyl compounds of formula IXa are isolated after the reaction as hydrobromides and are purified by crystallization or further reacted without purification.

Insofar as the compounds according to the present invention of formula I have a center of chirality, they can be present either as racemic mixtures or in the form of enantiomers. Racemic mixtures can be resolved into the enantiomers with the use of conventional methods.

Since the compounds of formula I possess basic centers, for the purpose of purification and/or for galenical reasons, they can be converted with using inorganic or organic acids into crystalline, pharmacologically acceptable salts. For example, hydrochloric acid, sulphuric acid, phosphoric acid, hydrobromic acid, acetic acid, tartaric acid, lactic acid, citric acid, malic acid, salicylic acid, ascorbic acid, malonic acid, fumaric acid, oxalic acid or succinic acid can be used. The acid addition salts are usually obtained in known manner by mixing the free bases or solutions thereof with the appropriate acid or a solution thereof in an organic solvent, for example a lower alcohol, such as methanol, ethanol or propan 2-ol, or a lower ketone, such as acetone or butan-2-one, or an ether, such as diethyl ether, diisopropyl ether, tetrahydrofuran or dioxan.

The compounds of formula I according to the present invention display useful pharmacological properties. In particular, they inhibit protein kinase C, a calcium- and phospholipid-dependent key enzyme, which plays a decisive part in the intracellular signal chain transduction (Y. Nishizuka, Science, 233, 305-312/1986) and is closely linked with he regulation of contractile, secretory and proliferative processes.

On the basis of these properties, the compounds according to the present invention can be used for the prevention and/or treatment of heart and blood vessel diseases, such as thromboses, arterioscleroses and hypertonias, of inflammatory processes, allergies, cancers and certain degenerative damage of the central nervous system.

Therefore, the present invention is also concerned with the use of the alkoxy-4(1H)-pyridone derivatives of formula I for the treatment of heart and blood vessel diseases, inflammatory processes, allergies, cancers and diseases of the central nervous system.

Surprisingly it has been found additionally that the compounds of formula I according to the present invention induce an endothelium-dependent smooth muscle relaxation.

The compounds of formula I according to the present invention can be administered orally or parenterally in liquid or solid form. As injection medium water is preferably used which contains the additives usual in the case of injection solutions, such as stabilizing agents, solubilizing agents or buffers.

Such additives include, for example, tartrate and citrate buffers, ethanol, complex formers (such as ethylenediamine-tetraacetic acid and the nontoxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol). Compositions suitable for oral administration can, if desired, contain additional flavoring and/or sweetening agents.

The individual dosages administered enterally or parenterally are in the range of from 0.5 to 1000 mg and preferably of from 1 to 100 mg.

The following Examples are given for the purpose of illustrating the present invention.

EXAMPLE 1

2-Hydroxymethyl-5-octadecyloxy-4-pyranone

A mixture of 56.8 g (0.4 mole) kojic acid, 55,3 g (0.4 mole) potassium carbonate, 133.3 g (0.4 mole) 1-octadecyl bromide, 1 g potassium iodide and 450 mL anhydrous dimethylformamide is stirred for 10 hours at 90° C.. After cooling, the mixture is mixed with 1.5 L of water, the precipitate formed is filtered off, well stirred up once with ethyl acetate, filtered off and recrystallized from propan-2-ol with the addition of active charcoal. There is obtained a colorless product: m.p. 71°-73° C.

In a manner analogous to that described in Example 1, there are obtained the following compounds:

EXAMPLE 2

2-Hydroxymethyl-5-tetradecyloxy-4-pyranone; m.p. 65°-68° C., recrystallized from propan-2-ol.

EXAMPLE 3

5-Eicosanyloxy-2-hydroxymethyl-4-pyranone; m.p. 81°-84° C., recrystallized from propan-2-ol.

EXAMPLE 4

5-Butyloxy-2-hydroxymethyl-4-pyranone 48.3 g (0.352 mole) 1-butyl bromide are added at ambient temperature, with vigorous stirring, to a mixture of 50 g (0.352 mole) kojic acid, 48.7 g (0.352 mole) potassium carbonate, 1 g potassium iodide and 420 mL anhydrous dimethylformamide. Thereafter, the reaction mixture is stirred for 3 hours at 90° C. After cooling, the solvent is removed under vacuum and the residue is mixed with water and extracted with dichloromethane. The organic phase is separated off and dried, the solvent is evaporated and the residue is recrystallized from ethyl acetate. There is obtained a solid, colorless product; m.p. 68°-73° C.

In a manner analogous to that described in Example 4, there is obtained the following compound:

EXAMPLE 5

5-Decyloxy-2-hydroxymethyl-4-pyranone; m.p. 46°-50° C., recrystallized from ethyl acetate.

EXAMPLE 6

2-Hydroxymethyl-5-(9 cis-octadecenyloxy)-4-pyranone

A mixture of 14.2 g (0.1 mole) kojic acid, 13.8 g (0.1 mole) potassium carbonate, 1 g potassium iodide, 33.14 g (0.1 mole) 1-bromo-9-cis octadecene and 120 mL anhydrous dimethylformamide is stirred for 3 hours at 90° C. After cooling, the solvent is removed under vacuum and the residue is mixed with water and extracted with dichloromethane. The organic phase is separated off, dried and evaporated. The residue is purified by column chromatography on silica gel with dichloromethane-methanol (100:1 v/v) to give a yellow oil, $^1$H-NMR (90 MHz; CDCl$_3$) (ppm): 0.85 (t, 3H), 1.30 (s, 22H); 1.7-2.(m, 6H); 3.8 (t, 2H): 4.2 (t, 1H); 4.4 (d, 2H); 5.3 (t, 2H); 6.5 (s, 1H); 7.55 (s, 1H).

In a manner analogous to that described in Example 6, there are obtained the following compounds:

EXAMPLE 7

2-Hydroxymethyl-5-(2-octyldecyloxy)-4-pyranone, yellow oil, IR (KBr): 1640 (C=O).

EXAMPLE 8

5-[2-(1-Adamantyl)ethoxy]-2-hydroxymethyl-4-pyranon; m.p. 155°-157° C. from 2-propanol/water.

EXAMPLE 9

1-Benzyl-2-hydroxymethyl-5-octadecyloxy-4(1H)-pyridone

A mixture of 50.0 g (0.127 mole) 2-hydroxymethyl-5-octadecyloxy-4 pyranone and 70 mL benzylamine is stirred for 2 hours at 100°-110° C. After cooling to about 50° C., the dark solution is mixed with 400 mL water and stirred. The precipitate thus formed is filtered off, washed, dried and recrystallized from propan-2-ol with the addition of active charcoal, colorless crystals thereby being obtained; m.p. 120°-121° C.

In a manner analogous to that described in Example 9, there are obtained the following compounds:

EXAMPLE 10

1-Benzyl-5-butoxy-2-hydroxymethyl-4(1H)-pyridone; m.p. 123°-124° C., recrystallized from propan-2-ol.

EXAMPLE 11

1-Benzyl-5-decyloxy-2-hydroxymethyl-4(1H)-pyridone; m.p. 128°-129° C., recrystallized from propan-2-ol.

EXAMPLE 12

1-Benzyl-2-hydroxymethyl 5 tetradecyloxy-4(1H)-pyridone; m.p. 121°-123° C., recrystallized from propan-2-ol.

EXAMPLE 13

1-Benzyl-5-eicosanyloxy-2-hydroxyaethyl-4(1H)-pyridone; m.p. 120°-122° C., recrystallized from propan-2-ol.

EXAMPLE 14

1-Benzyl-2-hydroxymethyl-5-(9-cis-octadecenyloxy)-4(1H)-pyridone; m.p. 92°-93° C., recrystallized from ethanol.

EXAMPLE 15

2-Hydroxymethyl-1-(4-methylbenzyl)-5-octadecyloxy-4(1H)-pyridone; m.p. 122°-125° C., recrystallized from propan-2-ol.

EXAMPLE 16

1-(4-Chlorobenzyl)-2-hydroxymethyl-5-octadecyloxy-4(1H)-pyridone; m.p. 125°-127° C., recrystallized from propan-2-ol.

EXAMPLE 17

2-Hydroxymethyl-1-(4-methoxybenzyl)-5-octadecyloxy-4(1H)-pyridone; m.p. 120°-122° C., recrystallized from propan-2-ol.

EXAMPLE 18

2-Hydroxymethyl-1-(2-methoxybenzyl)-5-octadecyloxy-4(1H)-pyridone; m.p. 107°-110° C., recrystallized from diisopropyl ether/propan-2-ol.

EXAMPLE 19

1-Cyclohexylmethyl-2-hydroxymethyl-5-octadecyloxy-4(1H)-pyridone; m.p. 126°-128° C., recrystallized from propan-2-ol.

EXAMPLE 20

1-(4-Dimethylaminobenzyl)-2-hydroxymethyl-5-octadecyloxy-4(1H)-pyridone; m.p. 109°-114° C., recrystallized from ethanol.

EXAMPLE 21

1-(3-Dimethylaminopropyl)-2-hydroxymethyl-5-octadecyloxy-4(1H)-pyridone; m.p. 87 90° C., recrystallized from ethyl acetate.

EXAMPLE 22

1-(4-Benzyloxyphenyl)-2-hydroxymethyl-5-octadecyloxy-4(1H)-pyridone: m.p. 116°-120° C., stirred with ether.

EXAMPLE 23

1-Benzyl-2-hydroxymethyl-5-(2-octyldecyloxy-4(1H)-pyridone, yellow oil, IR (KBr): 1630 (C=O).

EXAMPLE 24

5-[2-(1-Adamantyl)ethoxy]-1-1-benzyl-2-hydroxymethyl-4(1H)-pyridone, Schmp. 246°-248° C., stirred with ether.

EXAMPLE 25

(±)-2-Hydroxymethyl-5-octadecyloxy 1-(1-phenylethyl)-4(1H)-pyridone

A mixture of 8.0 g (0.02 Mol) 2-hydroxymethyl-5-phenylethylamine, 1.5 g $Na_2CO_3$, 10 mL water and 100 mL ethanol is boiled under reflux for 72 hours. After cooling the solvent and the excess of amine is removed under vacuum and the residue is mixed with water and extracted with dichloromethane. The organic phase is dried over $Na_2SO_4$, evaporated and the obtained resin is purified by column chromatography on silica gel with dichloromethane with 1-2% methanol to give a yellow oil, which is changing to wax-like consistency. IR (KBr): 1630 (C=O), MS (m/l) 497 (M+).

In a manner analogous to that described in Example 25, there are obtained the following compounds:

EXAMPLE 26

(−)-2-Hydroxymethyl-5-octadecyloxy-1-(1-phenylethyl)-4(1H)-pyridone, wax-like, IR (KBr): 1630 (C=O), $[\infty]_D = -15,9°$ (C=2.42 methanol).

EXAMPLE 27

(+)-2-Hydroxymethyl-5-octadecyloxy-1-(1-phenylethyl)-4(1H)-pyridone, wax-like, IR (KBr): 1630 (C=O), $[\infty]_D = 16,5°$ (C=2.01 methanol).

EXAMPLE 28

2-Hydroxymethyl-5-octadecyloxy-1-propyl-4(1H) pyridone

A mixture of 20.0 g (51 mMole) 2-hydroxymethyl-5-octadecyloxy-4-pyranone and 30 mL of a 40% solution of propylamine in ethanol is heated in an autoclave at 100°-110° C. for 5 hours. After cooling, the crystallizate formed is taken up in water, stirred, filtered off, dried and recrystallized from ethyl acetate, colorless crystals thereby being obtained; m.p 120°-121° C.

In a manner analogous to that described in Example 28, there is obtained the following compound:

EXAMPLE 29

2-Hydroxymethyl-1-methyl-5-octadecyloxy-4(1H)-pyridone; m.p. 96°-99° C., recrystallized from propan-2-ol.

EXAMPLE 30

2-Hydroxymethyl-5-octadecyloxy 1-phenyl-4(1H)-pyridone 5.0 g (12 mMole) 2-hydroxymethyl-5 octadecyloxy-4-pyranone are suspended in 90 mL water and 2 mL concentrated hydrochloric acid and mixed with 4.0 g (43 mMole) aniline. The mixture is heated under reflux for 24 hours, cooled and the precipitate formed is separated from the aqueous solution and recrystallized from ethyl acetate, an almost colorless product being obtained; m.p. 67°-72° C. In a manner analogous to that described in Example 30, there is obtained the following compound:

EXAMPLE 31

1-(4 Benzyloxyphenyl)-2-hydroxymethyl-5-octadecyloxy-4(1H) pyridone; m.p. 68°-70° C.: further worked up in crude form.

EXAMPLE 32

1-Benzyl-2-bromomethyl-5-octadecyloxy-4(1H)-pyridone hydrobromide 5.1 mL (0.1 mole) Bromine are added dropwise at ambient temperature, while stirring, to a solution of 26.5 g (0.1 mole) triphenylphosphine in 600 mL anhydrous toluene, a white crystalline precipitate thereby being formed. After further stirring for 20 minutes at ambient temperature, 48.17 g (0.1 mole) 1-benzyl-2-hydroxymethyl-5-octadecyloxy-4(1H)-pyridone are added thereto in portions. Thereafter, the reaction mixture is stirred for 2 hours at 70° C., cooled and the precipitated product is filtered off, washed with toluene, dried and recrystallized from propan-2-ol, pale beige crystals being obtained; m.p. 92°-95° C.

In a manner analogous to that described in Example 32, there are obtained the following compounds:

EXAMPLE 33

1-Benzyl-2-bromomethyl-5 butoxy-4(1H)-pyridone hydrobromide; syrupy; further worked up in crude form.

EXAMPLE 34

1-Benzyl-2-bromomethyl-5-decyloxy-4(1H)-pyridone hydrobromide; syrupy; further worked up in crude form.

EXAMPLE 35

1-Benzyl-2-bromomethyl-5 tetradecyloxy-4(1H)-pyridone hydrobromide; m.p. 135°-137° C., stirred up with acetone.

EXAMPLE 36

1-Benzyl-2-bromomethyl-5-eicosanyloxy-4(1H)-pyridone hydrobromide; m.p. 97°-100° C., stirred up with acetone.

EXAMPLE 37

1-Benzyl-2-bromomethyl-5-(9-cis-octadecenyloxy)-4(1H)-pyridone hydrobromide.

EXAMPLE 38

2-Bromomethyl-1-(4-methylbenzyl)-5-octadecyloxy)-4(1H)-pyridone hydrobromide: m.p. 106 110° C., recrystallized from toluene.

EXAMPLE 39

2-Bromomethyl-1-(4-chlorobenzyl)-5-octadecyloxy-4(1H)-pyridone hydrobromide; m.p. 138°-148° C., stirred up with toluene.

EXAMPLE 40

2-Bromomethyl-1-(4-methoxybenzyl)-5-octadecyloxy-4(1H)-pyridone hydrobromide: m.p. 94°-97° C., recrystallized from toluene.

EXAMPLE 41

2-Bromomethyl-1-(2-methoxybenzyl)-5-octadecyloxy-4(1H)-pyridone hydrobromide; further worked up in crude form.

EXAMPLE 42

2-Bromomethyl-1-cyclohexylmethyl-5 octadecyloxy-4(1H)-pyridone hydrobromide; further worked up in crude form.

EXAMPLE 43

2-Bromomethyl-1-(4-dimethylaminobenzyl)-5-octadecyloxy-4(1H)-pyridone hydrobromide; further worked up in crude form.

EXAMPLE 44

2-Bromomethyl-5-octadecyloxy-1-propyl-4(1H)-pyridone hydrobromide; m.p. 85°-87° C., recrystallized from acetone.

EXAMPLE 45

2-Bromomethyl-1-methyl-5-octadecyloxy-4(1H)-pyridone hydrobromide; m.p. 147 148° C., recrystallized from acetone.

EXAMPLE 46

2-Bromomethyl-5-octadecyloxy-1-phenyl-4(1H)-pyridone hydrobromide; m.p. 136°-140° C., recrystallized from propan-2-ol.

EXAMPLE 47

1-(4-Benzyloxybenzyl)-2-bromomethyl-5-octadecyloxy-4(1H)-pyridone hydrobromide, used as crude product.

EXAMPLE 48

1 (4-Benzyloxyphenyl) 2-bromomethyl-5-octadecyloxy-4(1H)-pyridone hydrobromide, used as crude product.

EXAMPLE 49

1-Benzyl-2-bromomethyl-5-(2-octyldecyloxy)-4(1H)-pyridone.hydrobromide

A solution of 0.25 mL (5 mMol) from in 2.5 mL dichloromethane is added dropwise at ambient temperature to a solution of 1.3 g (5 mMol) triphenylphosphin in 10 mL dichloromethane while stirring. The stirring is continued for 20 min and than a solution of 2.4 g (5 mMol) 2-hydroxymethyl-5-(2-octyldecyloxy)-4-pyranone in 10 mL dichloromethane is added dropwise. The mixture is boiled under reflux for 4 hours. After cooling the solvent is distilled off, the residue mixed with ether, the obtained crystallizate filtered off, dried and without further purification used.

In a manner analogous to that described in Example 49, there are obtained the following compounds:

EXAMPLE 50

5-[2-(1-Adamantyl)ethoxy]-1-benzyl-2-bromomethyl-4(1H)-pyridone.hydrobromide; m.p. 200°–203° C. from 2-propanol.

EXAMPLE 51

($\pm$)-2-Bromomethyl-5-octadecyloxy-1-(1-phenylethyl)-4(1H)-pyridone.hydrobromide, used as crude product.

EXAMPLE 52

($-$)-2-Bromomethyl-5-octadecyloxy-1-(1-phenylethyl)-4(1H)-pyridone.hydrobromide, used as crude product.

EXAMPLE 53

($+$)-2-Bromomethyl-5-octadecyloxy-1-(1-phenylethyl)-4(1H)-pyridone.hydrobromide, used as crude product.

EXAMPLE 54

1-Benzyl-2-N-(3-dimethylaminopropyl)-aminomethyl]-5-octadecyloxy-4(1H)-pyridone dioxalate 3.1 g (5 mMole) 1-benzyl-2-bromomethyl 5-octadecyloxy-4(1H)-pyridone hydrobromide are added in portions to a solution of 2.5 g (25 mMole) 3-dimethylamino 1-propylamine in 30 mL propan-2-ol, while stirring at ambient temperature. The mixture obtained is stirred for 1.5 hours at 60° C., cooled, evaporated under vacuum and the residue is mixed with water and extracted with dichloromethane. The dichloromethane solution is dried over anhydrous sodium sulphate, filtered and evaporated under vacuum to give an oil-like solid material. This is purified by column chromatography over silica gel with elution with dichloromethane/ammonia-saturated methanol (9:1 v/v) and then dissolved in methanol. The solution is mixed with a solution of oxalic acid in methanol and the precipitated salt is filtered off with suction and recrystallized from methanol/water (2.5:1 v/v). Colorless crystals being obtained; m.p. 161°–164° C.

In a manner analogous to that described in Example 54, there are obtained the following compounds:

EXAMPLE 55

1-Benzyl-2-[N-(3-hydroxypropyl)-aminomethyl]-5-octadecyloxy-4(1H)-pyridone; m.p. 89°–91° C., recrystallized from diisopropyl ether/propan-2-ol.

EXAMPLE 56

2-[N-(3-Dimethylaminopropyl)-aminomethyl]-1-methyl 5-octadecyloxy-4(1H)-pyridone trihydrochloride hemihydrate; m.p. 230° C. (decomp.), recrystallized from ethanol.

EXAMPLE 57

1-Benzyl-2-[N-(2-dimethylaminoethyl)-N-methylaminomethyl]-5-octadecyloxy-4(1H)-pyridone trihydrochloride; m.p. 172°–174° C., recrystallized from propan-2-ol.

EXAMPLE 58

2-[N (3-Hydroxypropyl)aminomethyl]-1-methyl-5-octadecyloxy-4(1H)-pyridone; m.p. 79°–82° C., digested with diethyl ether.

EXAMPLE 59

2-[N-(3-Dimethylaminopropyl)aminomethyl-5-octadecyloxy-1-propyl-4(1H) pyridone dioxalate; m.p. 171°–172° C., recrystallized from methanol.

EXAMPLE 60

2-[N-(3-Aminopropyl)-aminomethyl]-1-methyl-5-octadecyloxy-4(1H)-pyridone trihydrochloride: m.p. 212°–215° C., recrystallized from ethanol.

EXAMPLE 61

2-[N-(3-Aminopropyl)-aminomethyl]-1-benzyl-5-octadecyloxy 4(1H)-pyridone trihydrochloride; m.p. 180°–183° C., recrystallized from ethanol.

EXAMPLE 62

2-[N-(3-Aminopropyl)aminomethyl]-1-propyl-5-octadecyloxy-4(1H)-pyridone trihydrochloride; m.p. 204°–205° C., recrystallized from propan-2-ol/methanol.

EXAMPLE 63

1-Benzyl-5-butyloxy-2-N (3-dimethylaminopropyl)-aminomethyl]-4(1H)-pyridone dioxalate ¾hydrate; m.p. 179°–180° C., recrystallized from propan-2-ol.

EXAMPLE 64

1-Benzyl-5-decyloxy-2-[N-(3-dimethylaminopropyl)-aminomethyl]4(1H)-pyridone dioxalate hemihydrate; m.p. 166°–67° C., recrystallized from propan-2 ol.

EXAMPLE 65

1-Benzyl-2-N (3-dimethylaminopropyl)aminomethyl]-5-tetradecyloxy-4(1H)-pyridone dioxalate monohydrate; m.p. 163°–167° C. recrystallized from methanol/water.

EXAMPLE 66

1-Benzyl-2-[N-(3-dimethylaminopropyl)aminomethyl]-5-eicosanyloxy 4(1H)-pyridone dioxalate monohydrate; m.p. 165° C., recrystallized from propan-2-ol/water.

EXAMPLE 67

2-[N-(2-Aminoethyl)aminomethyl]-1-benzyl-5-octadecyloxy-4(1H)-pyridone ½hydrate; m.p. 87–89° C., recrystallized from diisopropyl ether.

EXAMPLE 68

1-Cyclohexylmethyl-2-[N-(3-dimethylaminopropyl)-aminomethyl]5-octadecyloxy-4(1H)-pyridone difumarate; m.p. 142°–145° C., recrystallized from ethanol.

EXAMPLE 69

1-(4-Chlorobenzyl)-2-[N-(3-dimethylamino-propyl)-aminomethyl]-5 octadecyloxy-4(1H)-pyridone difumarate 1.25 hydrate; m.p. 121°–123° C., recrystallized from ethanol.

EXAMPLE 70

2-[N-(3-Dimethylaminopropyl)aminomethyl]-5-octadecyloxy-1-phenyl-4(1H)-pyridone; diisopropyl ether.

EXAMPLE 71

1-Benzyl-2-[N-(3-N benzyl-N-methylaminopropyl)-aminomethyl]-5 octadecyloxy-4(1H)-pyridone difumarate; m.p. 140°–142° C., recrystallized from ethanol.

EXAMPLE 72

2-[N-(3 Dimethylaminopropyl)aminomethyl]-1-(4-methoxybenzyl)-5-octadecyloxy-4(1H)-pyridone trihydrochloride monohydrate; m.p. 140°–145° C., recrystallized from butan-2-one/propan-2-ol.

EXAMPLE 73

1-Benzyl-2-dimethylaminomethyl-5-octadecyloxy-4(1H)-pyridone oxalate hemihydrate; m.p. 138°–139° C., recrystallized from propan-2-ol.

EXAMPLE 74

2-[N-(3-Dimethylaminopropyl)aminomethyl]-1-(2-methoxybenzyl)-5-octadecyloxy-4(1H)-pyridone difumarat m.p. 108°–112° C., recrystallized from propan-2-ol.

EXAMPLE 75

1-Benzyl-2-(N-benzyl N-methylaminomethyl)-5-octadecyloxy-4(1H)-pyridone; m.p. 59°–61° C., recrystallized from ligroin.

EXAMPLE 76

2-[N-(3-Dimethylaminopropyl)aminomethyl]-1-(4-methylbenzyl)-5-octadecyloxy-4(1H)-pyridone trihydrochloride hemihydrate; m.p. 141°–148° C., recrystallized from ethyl acetate/propan-2-ol.

EXAMPLE 77

2-[N-(4-Aminobutyl)aminomethyl]-1-benzyl-5-octadecyloxy-4(1H)-pyridone trihydrochloride; m.p. 179°–183° C., recrystallized from diethyl ether/ethyl acetate.

EXAMPLE 78

1-Benzyl-2-[N-(3-dimethylaminopropyl)aminomethyl]-5-(9-cis-octadecenyloxy)-4(1H)-pyridone.trihydrochloride.½H$_2$O; m.p. 181°–185° C. from ethyl acetate.

EXAMPLE 79

1-(4-Benzyloxyphenyl)-2-[N-(3-dimethylaminopropyl)-aminomethyl]-5-octadecyloxy-4(1H)-pyridone: m.p. 43°–47° C.

EXAMPLE 80

1-(4-Benzyloxyphenyl)-2-[N-(3-dimethylaminopropyl)-aminomethyl]-5-octadecyloxy-4(1H)-pyridone.difumarate.2,5 H$_2$O; m.p. 103°–109° C. from propanol/ethyl acetate.

EXAMPLE 81

1-Benzyl-2-[N-(3-dimethylaminopropyl)aminomethyl]-5-(2-octyldecyloxy)-4(1H)-pyridone trihydrochloride.¾H$_2$O; m.p. 168°–172° C. from methylethylketon/2-propanol.

EXAMPLE 82

5-(2-Adamantylethoxy)-1-benzyl-2-[N-(3-dimethylaminopropyl)aminomethyl]-4(1H)-pyridone, yellow oil, MS (m/l) 477 M+.

EXAMPLE 83

(±)-1 Benzyl-5-octadecyloxy)-2-{N-[3-(1 phenylethyl)aminopropyl]-aminomethyl}-4(1H)-pyridone.trihydrochloride; m.p. 125°–127° C. mixed with toluene.

EXAMPLE 84

2-N-(3-Dimethylaminopropyl)-aminomethyl]-1-(4-hydroxybenzyl)-5-octadecyloxy-4(1H)-pyridone.dihydrochloride.2 H$_2$O To a solution 1.0 g (1.5 mMol) 1-(4-benzyloxybenzyl)-2-[N-(3-dimethylaminopropyl)-aminomethyl]-5-octadexyloxy-4(1H)-pyridone in 30 mL absolute ethanol are added 0.25 g palladium on charcoal (10% ig, oxide-type) and the mixture is hydrogenated at ambient temperature and normal pressure. After filtration of the catalyst the solvent is distilled off and the residue purified by column chromatography on silica gel with dichloromethane with 3–6% methanol saturated with gaseous NH$_3$.gesättigt säulenchromatographiert. The obtained reaction product (wax-like compound with R$_f$=0,55, silica gel, dichloromethan/methanol, saturated with NH$_3$ 4:1) is mixed with methanol, saturated with gaseous HCl, to obtain the salt form. The solvent is distilled off and the residue recrystallized from 2-propanol/ethyl acetate. There are obtained colorless crystals; m.p. 153°–156° C.

In a manner analogous to that described in Example 84, there is obtained the following compound:

EXAMPLE 85

2-[N-(3-Dimethylaminopropyl)aminomethyl]-1-(4-hydroxyphenyl)-5-octadecyloxy-4(1H)-pyridone.trihydrochloride.0,5 H$_2$O; m.p. 236°–237° C. from methanol.

EXAMPLE 86

1-(1-Benzyl-5-octadecyloxy-4(1H)-pyridon-2-yl)-methyl]-4-cyano-4-phenylpiperidine dihydrochloride A solution of 2.0 g (9 mMole) 4 cyano-4-phenylpiperidine hydrochloride in 40 mL ethanol is mixed with 4.8 mL (35 mMole) triethylamine. 5.0 g (8 mMole) 1-benzyl-2-bromomethyl-5-octadecyloxy-4(1H)-pyridone hydrobromide are added in portions to this mixture, while stirring at ambient temperature. The reaction mixture is stirred for 3 hours at 60° C., the solvent is removed under vacuum, the residue is mixed with water and dichloromethane, stirred and the organic phase is separated off, dried over anhydrous sodium sulphate and evaporated. The residue is purified by column chromatography on silica gel with dichloromethane/methanol (97:3 v/v). There is obtained an oily product. 1.0 g (1.5 mMole) of this substance is dissolved in 30 mL ethyl acetate and mixed with diethyl ether saturated with gaseous hydrogen chloride for salt formation. The precipitated salt is recrystallized from ethyl acetate/propan-2 ol (6:1 v/v), colorless crystals being obtained (m.p. 106°–112° C.). The solid material contains about ¾ mole of water per mole of the said product.

In a manner analogous to that described in Example 86, there are obtained the following compounds:

EXAMPLE 87

1-[(1-Benzyl-5-octadecyloxy-4(1H)-pyridon-2-yl)-methyl]-4 methoxycarbonyl-2-methyl-piperazine dihydrochloride ½hydrate; m.p. 111°–117° C., recrystallized from ethyl acetate/propan-2-ol.

EXAMPLE 88

1-[(1-Benzyl-5-octadecyloxy-4(1H)-pyridon-2-yl)-methyl]-4 benzylpiperazine; m.p. 78 80° C., recrystallized from diisopropyl ether.

EXAMPLE 89

1-Benzyl-2-[N-(3-dimethylaminopropyl)-N-methylaminomethyl]-5-octadecyloxy-4(1H)-pyridone trihydrochloride; m.p.186°–189° C., recrystallized from propan-2-ol/ethanol.

EXAMPLE 90

1-(1-Benzyl-5-octadecyloxy-4(1H)-pyridon-2-yl)-methyl]-4-diphenylmethylpiperazine sesquioxalate monohydrate; m.p. 124 129° C., recrystallized from ethyl acetate.

EXAMPLE 91

1-[(1-Benzyl-5-octadecyloxy-4(1H)-pyridone-2-yl)-methyl]4-phenylpiperzine.dihydrochloride.H$_2$O; m.p. 80° C. (sintering) from ethyl acetate/methanol.

EXAMPLE 92

1-[(1-Benzyl-5-octadecyloxy-4(1H)-pyridone-2-yl)-methyl]-4-(2-pyrimidinyl)piperazine; m.p. 96 97° C. from diisopropylether/2-propanol.

EXAMPLE 93

1-[(1-Benzyl-5-octadecyloxy-4(1H)-pyridone-2-yl)-methyl]-4-benzylpiperazine.dioxalate.½H$_2$O; m.p. 133°–136° C. from ethanol.

EXAMPLE 94

1-[(1-Benzyl-5-octadecyloxy-4(1H)-pyridone-2-yl)-methyl]4-(2-phenylethyl)piperazine.trihydrochloride.½ H$_2$O: m.p. 161°–164° C. from ethylacetate/2-propanol.

EXAMPLE 95

1-[(1-Benzyl-5-decyloxy-4(1H)-pyridone-2-yl)-methyl]-4-(2-phenylethyl)piperazine.dihydrochloride; m.p. 161°–164° C. from ethylacetate/2-propanol.

EXAMPLE 96

1-[(1-Benzyl-5-benzyloxy-4(1H)-pyridone-2-yl)-methyl]-4-benzylpiperazine.trihydrochloride; m.p. 189°–191° C. from ethylacetate/2 propanol.

EXAMPLE 97

(±)-1-[(1-Benzyl-5-octadecyloxy-4(1H)-pyridone-2-yl)-methyl]-4-(1-phenylethyl)pioerazine.trihydrochloride ¾H$_2$O; m.p. 167°–170° C. from acetonitrile/2-propanol.

EXAMPLE 98

(±)-1-(5-Octadecyloxy-1-(1-phenylethyl)-4(1H)-pyridone-2-yl)-methyl]-4-benzylpiperazine; m.p. 76°–78° C. from diisopropylether.

EXAMPLE 99

(−)-1-[(5-Octadecyloxy-1-(1-phenylethyl)-4(1H)-pyridone-2-yl)-methyl]-4-benzylpiperazine; m.p. 60°–61° C. from diisopropylether, [∞]$_D$= −2,3° (C=2,06 methanol).

EXAMPLE 100

(+)-1-(5-Octadecyloxy-1-(1-phenylethyl)-4(1H)-pyridone-2-yl)-methyl]-4-benzylpiperazine; m.p. 60°–61° C. from diisopropylether, [∞]$_D$= +2,4° (C=2,01 methanol).

EXAMPLE 101

1-[(1-Benzyl-5-octadecyloxy-4(1H)-pyridon-2-yl)-methyl]-4-aminomethyl-4-phenylpiperidine trihydrochloride 2.7 g (4.1 mMole) 1-[(1-benzyl-5-octadecyloxy-4(1H)-pyridon-2-yl)-methyl]-4-cyano-4-phenylpiperidine are mixed with 60 mL methanol saturated with gaseous ammonia and 1 g Raney nickel and hydrogenated with hydrogen in an autoclave at 60° C. and 60 bar pressure. After 6 hours, the reaction is finished. After filtering off the catalyst with suction, the pale yellow solution obtained is evaporated under vacuum and the residue chromatographed on a column of silica gel with dichloromethane/methanol saturated with ammonia (97:3 v/v). The reaction product thus obtained (oily substance with the R$_f$=0.5, silica gel, dichloromethane/methanol saturated with ammonia (9:1 v/v)) is dissolved in ethyl acetate and mixed with diethyl ether saturated with gaseous hydrogen chloride for salt formation. The precipitated salt is recrystallized from butan-2-one/propan-2-ol (10:1 v/v), colorless crystals being obtained; m.p. 192°–197° C. The solid material contains about 1.25 mole of water per mole of the said product.

EXAMPLE 102

(±)-1-(1-Benzyl-5 octadecyloxy-4(1H)-pyridon-2-yl)-methyl]-2-methyl-piperazine fumarate A mixture of 2 g (3.2 mMole) (±)-1-[(1-benzyl-5-octadecyloxy 4(1H)-pyridon-2-yl)-methyl]-4-methoxycarbonyl-2-methylpiperazine, 5 mL 33% hydrogen bromide/acetic acid and 5 mL acetic acid is stirred for 2 hours in a closed vessel. After stripping off the main amount of the solvent under vacuum, the residue is mixed with water, rendered alkaline with a 2N aqueous solution of sodium hydroxide and extracted with dichloromethane. The organic phase is separated off, dried over anhydrous sodium sulphate and evaporated. The resin obtained is purified by chromatography on a column of silica gel with dichloromethane/methanol saturated with gaseous ammonia (97:3 v/v). The reaction product thereby obtained (oily substance with the R$_f$=0.2; silica gel, dichloromethane/methanol saturated with gaseous ammonia 9:1 v/v) is dissolved in propan-2-ol and mixed with a solution of fumaric acid in propan-2-ol. After standing for 24 hours, the clear solution is evaporated and the salt is recrystallized from butan-2-one, colorless crystals being obtained; m.p. 151°–155°

C. The solid material contains about 1 mole of water per mole of the said product.

EXAMPLE 103

1-Benzyl-2-(3-dimethylaminopropoxymethyl)-5-octadecyloxy-4(1H)-pyridone dihydrochloride 7.2 g (15 mMole) 1-Benzyl-2-hydroxymethoxy-5-octadecyloxy-4(1H)-pyridone are dissolved in 110 mL anhydrous dimethylformamide at 70° C. and mixed portionwise with 0.60 g (20 mMole) sodium hydride (80% in paraffin oil). After subsequently stirring for 1.5 hours at 70 to 80° C., a solution of 3.3 g (27.15 mMole) 3-dimethylaminopropyl chloride in 20 mL anhydrous dimethylformamide is added dropwise thereto. The reaction mixture is then stirred for 2 hours at 70° C. Thereafter, the solution is evaporated to dryness under vacuum and the residue is mixed with water and dichloromethane. The organic phase is separated off, dried over anhydrous sodium sulphate and evaporated. The residue is chromatographed on a column of silica gel with dichloromethane/methanol saturated with gaseous ammonia (97:3 v/v), an oily substance being obtained. 1.8 g (3.3 mMole) of this substance are dissolved in a mixture of 30 mL ethyl acetate and 3,5 mL propan-2-ol and mixed with diethyl ether saturated with gaseous hydrogen chloride for salt formation. The precipitated salt is recrystallized from ethyl acetate/propan-2-ol (3:1 v/v), colorless crystals being obtained; m.p. 155°–159° C. The solid material contains about ½ mole of water per mole of the said product.

In a manner analogous to that described in Example 103, there are obtained the following compounds:

EXAMPLE 104

2-(3-Dimethylaminopropoxymethyl)-1-methyl-5-octadecyloxy-4(1H)-pyridone dihydrochloride; m.p. 210°–216° C., recrystallized from propan-2-ol.

EXAMPLE 105

2-(3-Dimethylaminopropoxymethyl)-5-octadecyloxy-1-propyl-4(1H)-pyridone dihydrochloride ½hydrate; m.p. 127°–128° C., recrystallized from ethyl acetate/propan-2-ol.

EXAMPLE 106

2-(3-Dimethylaminopropoxymethyl)-1-(4-methylbenzyl)-5-octadecyloxy-4(1H)-pyridone dihydrochloride sesquihydrate; m.p, 87°–84° C., recrystallized from ethyl acetate/propan-2-ol.

EXAMPLE 107

2-(3-Dimethylaminopropoxymethyl)-1-(4-methoxybenzyl)-5-octadecyloxy-4(1H)-pyridone dihydrochloride ½hydrate; m.p. 144°–147° C., recrystallized from propan-2-ol.

EXAMPLE 108

1-Cyclohexylmethyl-2-(3-dimethylaminopropoxymethyl)-5-octadecyloxy-4(1H)-pyridone oxalate; m.p. 81°–84° C., recrystallized from ethyl acetate/propan-2-ol.

EXAMPLE 109

1-(4-Chlorobenzyl)-2-(3-dimethylaminopropoxymethyl)-5-octadecyloxy-4(1H)-pyridone dihydrochloride 2.5 hydrate; m.p. 70°–74° C., recrystallized from ethyl acetate/propan-2-ol.

EXAMPLE 110

2-(3-Dimethylaminopropoxymethyl)-1-(2-methoxybenzyl)-5-octadecyloxy-4(1H)-pyridone sesquihydrate; m.p. 89°–91° C., recrystallized from ethyl acetate/propan-2-ol.

EXAMPLE 111

3-1-Benzyl-5-octadecyloxy-4(1H)-pyridon-2-yl]-propionic acid nitrile hydrochloride

A. tert.-Butyl 3-1-benzyl-5-octadecyloxy-4(1H)-pyridon-2-yl]-2-cyanopropionate A solution of 21.2 g (0.15 mole) tert.-butyl cyanoacetate in 15 mL anhydrous dimethylformamide is added dropwise at ambient temperature, while stirring, to a solution of 17.0 g (0.15 mole) potassium tert.-butylate in 60 mL anhydrous dimethylformamide. The clear solution is warmed to 50° C. and a solution of 43.4 g (0.07 mole) 1-benzyl-2-bromomethyl-5-octadecyloxy-4(1H)-pyridone hydrobromide in 150 mL anhydrous dimethylformamide added thereto at this temperature in the course of 5 minutes. After stirring for 1 hour at 55° C., the reaction mixture is added to 1.2 L of water and extracted with ethyl acetate. The organic phase is separated off, dried over anhydrous sodium sulphate and evaporated. The oily residue is purified by chromatographing on a column of silica gel with dichloromethane/methanol (9:1 v/v) (R$_f$=0.60; silica gel, dichloromethane/methanol 9:1 v/v), a yellow, oily product being obtained.

B. 3-[1-Benzyl-5-octadecyloxy-4(1H)-pyridon-2-yl]-2-cyanopropionic acid 13.2 g (22 mMole) tert.-butyl 3-[1-benzyl-5-octadecyloxy-4(1H)-pyridon-3-yl]-2-cyanopropionate are mixed with 47 mL 0.5N potassium hydroxide in methanol and stirred for 3 days at ambient temperature. The solvent is removed under vacuum and the residue is dissolved in water and acidified with 2N hydrochloric acid. The precipitate obtained is filtered off with suction, washed with water and diethyl ether and dried, a solid, colorless product being obtained (m.p. 122°–124° C.) which is sufficiently pure for the further reaction.

C. 3-1-Benzyl-5-octadecyloxy-4(1H)-pyridon-2-yl]-propionic acid nitrile hydrochloride 4.1 g (7.4 mMole) 3-[1-Benzyl-5-octadecyloxy-4(1H)-pyridon-2-yl]-2-cyanopropionic acid are heated to 150° C. for 30 minutes. After cooling, the product is obtained as an oil which is sufficiently pure for the further reaction.

0.5 g (1 mMole) of the substance is dissolved in ethyl acetate and mixed with diethyl ether saturated with gaseous hydrogen chloride for salt formation. The precipitated salt is filtered off with suction and dried, a beige product being obtained; m.p. 98°–102° C.

In a manner analogous to that described in Example 111, there is obtained the following compound:

EXAMPLE 112

3-(1-Methyl-5-octadecyloxy-4(1H)-pyridon-2yl)-propionic acid nitrile; m.p. 85°-87° C., digested with diethyl ether.

EXAMPLE 113

3-[1-Benzyl-5-octadecyloxy-4(1H)-pyridon-2yl]-propylamine dihydrochloride 3.7 g (7.3 mMole) 3-[1 Benzyl-5-octadecyloxy-4(1H)-pyridon-2-yl]-propionic acid nitrile are mixed with 40 mL methanol saturated with gaseous ammonia and hydrogenated with hydrogen at 60° C. and 60 bar in an autoclave. After filtering off the catalyst, the solution is evaporated under vacuum and the oily residue chromatographed on a column of silica gel with dichloromethane/methanol saturated with ammonia (95:5 v/v). There are thus obtained 2.2 g (59% of theory) of oily substance ($R_f$=0.1, silica gel, dichloromethane/methanol saturated with ammonia 9:1 v/v) which is converted with ethereal hydrochloric acid into the hydrochloride which is then recrystallized from butan-2-one/propan 2-ol (4:1 v/v), colorless crystals being obtained; m.p. 138°-143° C.

EXAMPLE 114

Methyl 3-[1 benzyl-5-octadecyloxy-4(1H)-pyridon-2-yl]-propionate 3.0 g (6 mMole) 3-[1-Benzyl-5-octadecyloxy-4(1H)-pyridon-2-yl]propionic acid nitrile are dissolved in 30 mL methanol saturated with gaseous hydrogen chloride and left to stand for 3 days at ambient temperature in a closed vessel. After stripping off the solvent under vacuum, the residue is mixed with water, rendered alkaline with a dilute aqueous solution of sodium hydroxide and extracted with dichloromethane. The dichloromethane solution is dried over anhydrous sodium sulphate and evaporated. The wax obtained is recrystallized twice from diisopropyl ether, colorless crystals being obtained; m.p. 78°-81° C.

EXAMPLE 115 AND 116

3-[1-Benzyl-5-octadecyloxy-4(1H)-pyridon-2-yl]-propanol and
3-[1-benzyl-5-octadecyloxy-4(1H)-pyridon-2-yl]-propionic acid amide 5.0 g (10 mMole) 3-[1-Benzyl-5-octadecyloxy-4(1H)-pyridon-2-yl]-propionic acid nitrile in 30 mL propan-2-ol are mixed, while stirring at ambient temperature, with 2.5 g (6.6 mMole) sodium borohydride and the reaction mixture further stirred for 4 days at 80° C. After stripping off the solvent under vacuum, the residue is mixed with a dilute aqueous solution of sodium hydroxide and stirred for 30 minutes at 40° C. After cooling, it is extracted with dichloromethane, the organic phase is washed with water, dried and evaporated. The residue is chromatographed on a column of silica gel with dichloromethane/methanol. By elution with dichloromethane containing 1 to 5% methanol, there is obtained the crude 3-[1-benzyl-5-octadecyloxy-4(1H)-pyridon-2-yl]-propanol ($R_f$=0.30; silica gel, dichloromethane/methanol 9:1 v/v). After recrystallization from diisopropyl ether/propan-2-ol (4:1 v/v), there are obtained pale beige crystals; m.p. 87°-89° C.

By further elution of the column with dichloromethane containing 6 to 10% methanol, there is obtained crude 3-[1-benzyl-5-octadecyloxy-4(1H)-pyridon-2-yl]-propionic acid amide ($R_f$=0.40: silica gel; dichloromethane/methanol 9:1 v/v). After recrystallization from butan-2-one, there are obtained colorless crystals; m.p. 134°-136° C.

Inhibition of the activity of protein kinase C

For the clarification of the inhibiting influence of compounds of formula I according to the present invention on the calcium- and phospholipid-dependent protein kinase (PKC), this enzyme activity was enriched from rat brain. Using the purification steps described in the literature (J. Biol. Chem., 260, 15718-15722/1985), in the case of a purification consisting of two steps, there was utilized the property of the enzyme to bind to cell membranes in the presence of calcium and to be dissolved off again by calcium chelators (EGTA). In the first enrichment step, there took place the binding of the PKC to membranes of the rat brain and in the second step on so-called inside-out vesicles of erythrocytes. After dissolving off from the erythrocyte membranes and rebuffering, the PKC preparation was present in 10 mM HEPES, 1 mM DTT, 0.1% PEG 20000, pH 7.5. Under these conditions, it could be stored at −70° C. for several months without loss of activity.

The activity of the enzyme was determined via the incorporation of $P^{32}$-labelled phosphate into the protein histone H-1 (Sigma Type III) which can be phosphorylated by PKC.

The test thereby contains the following components: 50 mM HEPES-NaOH (pH 7.5), 5 mM magnesium chloride, 1 mM DTT, 4 μm. free calcium ions, 10 μMaTP, 1 μg phosphatidylserine, 0.2 μg 1,2-diolein, as well as 40 μg histone H 1 and optionally the test substance.

The batch is preincubated for 4 minutes at 30° C. and the reaction then started by the addition of 5 nM PKC. After incubating for 5 minutes at 30° C., the reaction is stopped with 10% TCA and the samples then filtered off. The phosphate incorporation is determined by Cerenkov counting in a scintillation counter. The kinase activity measured in the absence of the test substance was, in each case, taken as being 100% and the inhibiting action of the compounds of formula I referred thereto as percentages. The results obtained are set out in the following Table I.

Endothelium-dependent smooth muscle relaxation

Rabbit aorta rings are fixed in an organ bath filled with physiological salt solution (Krebs-Henseleit) between L-shaped wires. The solution is gassed with carbogen. Contractions are initiated by $3 \times 10^{-7}$ noradrenaline. When the tension has reached a stable plateau, compounds of the instant invention are added. The effect of the compounds first is tested on organ preparation with functioning endothelium. In an additional experiment in order to test whether the relaxation is endothelium-dependent the compounds are tested with aorta rings with damaged endothelium. For an endothelium-dependent relaxation, effected by the endothelium-derived relaxating factor (EDRF), the following characteristics are required: absence of the effect in preparations with damaged endothelium, no inhibition of the relaxation by indomethazine and inhibition of the relaxation by NDGA (nordihydro-guaiaretic acid), methylene blue and gossypol. These criteria are completely met by the compounds listed in Table II, and one can conclude, that the compounds of the instant invention act in an unexpected manner by the release of EDRF, and thereby relax vascular smooth muscle.

TABLE I

| Example No. | Inhibition of Protein Kinase C IC$_{50}$ (mol/mL) |
|---|---|
| 19 | 2.4 × 10$^{-6}$ |
| 54 | 1.4 × 10$^{-6}$ |
| 56 | 2.9 × 10$^{-6}$ |
| 57 | 1.9 × 10$^{-6}$ |
| 59 | 2.9 × 10$^{-6}$ |
| 60 | 2.7 × 10$^{-6}$ |
| 61 | 2.1 × 10$^{-6}$ |
| 65 | 6.5 × 10$^{-6}$ |
| 66 | 2.5 × 10$^{-6}$ |
| 68 | 1.9 × 10$^{-6}$ |
| 69 | 1.5 × 10$^{-6}$ |
| 70 | 2.2 × 10$^{-6}$ |
| 71 | 1.8 × 10$^{-6}$ |
| 72 | 3.6 × 10$^{-6}$ |
| 73 | 4.4 × 10$^{-6}$ |
| 74 | 2.1 × 10$^{-6}$ |
| 75 | 9.5 × 10$^{-6}$ |
| 76 | 1.9 × 10$^{-6}$ |
| 77 | 2.3 × 10$^{-6}$ |
| 78 | 4.6 × 10$^{-6}$ |
| 79 | 2.2 × 10$^{-6}$ |
| 80 | 2.6 × 10$^{-6}$ |
| 83 | 2.6 × 10$^{-6}$ |
| 84 | 3.4 × 10$^{-6}$ |
| 85 | 5.8 × 10$^{-6}$ |
| 88 | 3.0 × 10$^{-6}$ |
| 89 | 1.8 × 10$^{-6}$ |
| 93 | 5.5 × 10$^{-6}$ |
| 94 | 2.4 × 10$^{-5}$ |
| 95 | 4.3 × 10$^{-6}$ |
| 97 | 4.4 × 10$^{-6}$ |
| 98 | 5.4 × 10$^{-6}$ |
| 99 | 5.2 × 10$^{-6}$ |
| 100 | 2.7 × 10$^{-6}$ |
| 101 | 1.5 × 10$^{-6}$ |
| 102 | 2.0 × 10$^{-6}$ |
| 103 | 4.0 × 10$^{-6}$ |
| 105 | 2.0 × 10$^{-6}$ |
| 106 | 2.4 × 10$^{-6}$ |
| 107 | 2.9 × 10$^{-6}$ |
| 108 | 2.9 × 10$^{-6}$ |
| 109 | 2.6 × 10$^{-6}$ |
| 114 | 9.0 × 10$^{-6}$ |
| 116 | 9.0 × 10$^{-6}$ |

TABLE II

| | Relaxation of Noradrenaline-Precontracted Aorta (3 × 10$^{-7}$ mol/L); EC$_{50}$: mol/L | |
|---|---|---|
| Example No. | Functioning Endothelium | Damaged Endothelium |
| 54 | 1.5 × 10$^{-5}$ | >10$^{-4}$ |
| 101 | 2 × 10$^{-5}$ | >10$^{-4}$ |
| 69 | 3 × 10$^{-5}$ | >10$^{-4}$ |
| 71 | 3 × 10$^{-6}$ | >10$^{-4}$ |
| 88 | 3.4 × 10$^{-6}$ | >10$^{-4}$ |
| Acetylcholine | 3 × 10$^{-8}$ | >10$^{-4}$ |

We claim:

1. A compound of formula

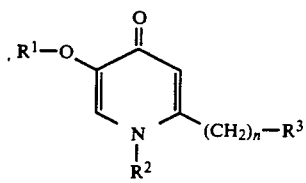

I or a pharmaceutically acceptable salt thereof wherein $R^1$ is straight or branched, saturated or unsaturated alkyl of from 10 to 22 carbon atoms or adamantyl ethyl;

$R^2$ is a straight or branched, saturated or unsaturated alkyl of from 1 to 5 carbon atoms, a cycloalkylmethyl radical having 5 to 7 carbon atoms in the cycloalkyl ring, phenyl, phenylalkyl with 1 to 5 carbon atoms in the straight or branched alkyl chain which phenyl is unsubstituted or substituted by halogen, hydroxyl, alkyl of from 1 to 5 carbon atoms, alkoxy of from 1 to 5 carbon atoms, dialkylamino having of from 1 to 5 carbon atoms, benzyloxy, or $R^2$ is an aminoalkyl of formula

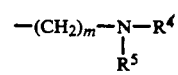

II wherein $R^4$ and $R^5$, are each independently hydrogen, alkyl of from 1 to 3 carbon atoms and m is an integer of from 2 to 5;

n is an integer of from 1 to 5; and $R^3$ is

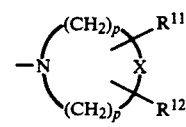

V wherein $R^{11}$ and $R^{12}$, are each independently hydrogen, alkyl of from 1 to 3 carbon atoms, phenyl, phenylalkyl with from 1 to 5 carbon atoms in the straight or branched alkyl chain, X is oxygen, or

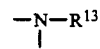

VI wherein $R^{13}$ is hydrogen, phenyl, phenylalkyl, diphenylalkyl with from 1 to 5 carbon atoms in the straight or branched alkyl chain, or X is

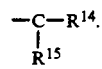

VII wherein $R^{14}$ is hydrogen, phenyl which is unsubstituted or substituted by halogen, hydroxyl, alkyl from 1 to 5 carbon atoms, alkoxy of from 1 to 5 carbon atoms, dialkylamino having of from 1 to 5 carbon atoms or benzyloxy and $R^{15}$ is hydrogen, hyrdoxyl, cyano, hydroxymethyl, aminomethyl, carboxamido, ethoxy or methoxycarbonyl and p and q, are each independently 2.

2. A compound of formula

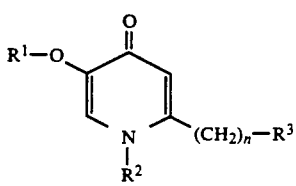

I or a pharmaceutically acceptable salt thereof wherein $R^1$ is straight or branched, saturated or unsaturated alkyl of from 1 to 22 carbon atoms or adamantylethyl;

$R^2$ is a straight or branched alkyl having from 1 to 4 carbon atoms, cycloalkylmethyl, unsubstituted phenyl, phenylalkyl with from 1 to 5 carbon atoms in the straight or branched alkyl chain which phenyl is monosubstituted by halogen, hydroxyl, methyl, benzyloxy, methoxy or dimethylamino;

n is an integer of from 1 to 3; and $R^3$ is

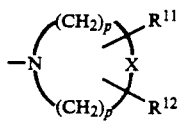 V in which $R^{11}$ and $R^{12}$, are each independently hydrogen or methyl, X is an amino radical of formula

 VI in which $R^{13}$ is hydrogen, phenyl, phenylalkyl, or diphenylalkyl with from 1 to 5 carbon atoms in the straight or branched alkyl chain or X is formula

 VII in which $R^{14}$ is phenyl, $R^{15}$ is cyano or aminomethyl, and p and q are each 2.

3. A compound of formula

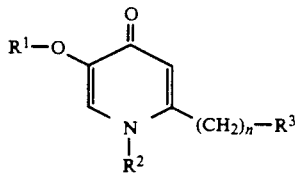 I or a pharmaceutically acceptable salt thereof wherein n is 1, 2 or 3;

$R^1$ is a decyl, tetradecyl, eicosanyl, octadecenyl, octadecyl, 2-octyldecyl or adamantylethyl;

$R^2$ is a propyl, methyl, phenyl, benzyl, methylbenzyl, chlorobenzyl, methoxybenzyl, cyclohexylmethyl, dimethylaminobenzyl, dimethylaminopropyl, benzyloxybenzyl, benzyloxyphenyl, phenylethyl, hydroxybenzyl or hydroxyphenyl; and $R^3$ is methoxycarbonylmethyl piperazino, benzylpiperazino, diphenylmethylpiperazino, aminomethylphenylpiperidino, phenylpiperazino, phenylethylpiperazino, pyrimidinylpiperazino or methylpiperazino.

4. A compound selected from
1-[(1-Benzyl-5-octadecyloxy-4(1H)-pyridon-2-yl)-methyl]-4-cyano-4-cyano-4-phenylpiperidine dihydrochloride,
1-[(1-Benzyl-5-octadecyloxy-4(1H)-pyridon-2-yl)-methyl]-4-methoxycarbonyl-2-methyl-piperazine dihydrochloride ¾hydrate,
1-[(1-Benzyl-5-octadecyloxy-4(1H)-pyridon-2-yl)-methyl]-4-piperazine,
1-[(1-Benzyl-5-octadecyloxy-4(1H)-pyridon-2-yl)-methyl]-4-diphenylmethylpiperazine sesquixalate monohydrate,
1-[(1-Benzyl-5-octadecyloxy-4(1H)-pyridon-2-yl)-methyl]-4-phenylpiperidine.dihydrochloride.H₂O,
1-[(1-Benzyl-5-octadecyloxy-4(1H)-pyridon-2-yl)-methyl]-4-(2-pyrimidinyl)piperazine,
1-[(1-Benzyl-5-octadecyloxy-4(1H)-pyridon-2-yl)-methyl]-4-benzylpiperazine.dioxalate.½H₂O,
1-[(1-Benzyl-5-octadecyloxy-4(1H)-pyridon-2-yl)-methyl]-4-(2-phenylethyl)piperzine.trihydrochloride.½H₂O,
1-[(1-Benzyl-5-octadecyloxy-4(1H)-pyridon-2-yl)-methyl]-4-(2-phenylethyl)piperidine.dihydrochloride,
(±)-1-[(1-Benzyl-5-ocatdecyloxy-4(1H)-pyridone-2-yl)-methyl]-4-(1-phenylethyl)-piperazine.trihydrochloride ⅔H₂O,
(±)-1-[(5-Octadecyloxy-1-(1-phenylethyl)-4(1H)-pyridone-2-yl)-methyl]-4-benzylpiperazine,
(−)-1-[(5-Octadecyloxy-1-(1-phenylethyl)-4(1H)-pyridone-2-yl)-methyl]-4-benzylpiperazine,
(+)-1-[(5-Octadecyloxy-1-(1-phenylethyl)-4(1HO-pyridone-2-yl)-methyl]-4-benzylpiperazine,
1-[(1-Benzyl-5-octadecyloxy-4(1H)-pyridon-2-yl)-methyl]-4-aminoethyl-4-phenylpiperidine trihydrochloride, and
(±)-1-[(1-Benzyl-5-octadecyloxy-4(1H)-pyridon-2-yl)methyl]-2-methylpiperazine fumarate.

5. A pharmaceutical composition for treating and/or preventing heart and blood vessel diseases comprising an effective amount of a compound according to claim 1 in admixture with a pharmaceutically acceptable carrier.

6. A method for treating and/or preventing heart and blood vessel diseases which comprises administering to a mammal in need of such treatment a pharmaceutical composition according to claim 5.

* * * * *

UNITED STATES PATENT AND TRADEMARK OFFICE
CERTIFICATE OF CORRECTION

PATENT NO. : 5,322,844
DATED : June 21, 1994
INVENTOR(S) : Julian Aranda, et al

It is certified that error appears in the above-indentified patent and that said Letters Patent is hereby corrected as shown below:

Column 32, lines 26-30

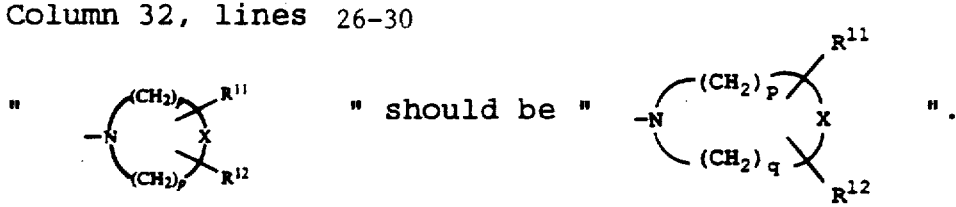

Column 32, line 43, insert after "chain" the following: "and where in the phenyl ring from 1 to 3 CH- groups may be substituted by nitrogen".

Column 32, line 55, "hyrdoxyl" should read "hydroxyl".

Column 33, line 1, insert "a" after "$R^1$ is".

Column 33, line 5, "cycloalkylmethyl" should read "cyclohexylmethyl".

Column 33, lines 14-18

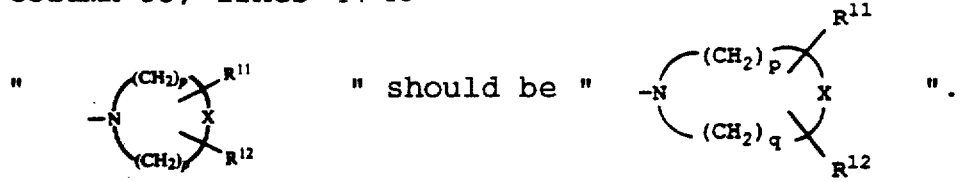

Column 34, line 10, delete the second "4-cyano-".

UNITED STATES PATENT AND TRADEMARK OFFICE
CERTIFICATE OF CORRECTION

PATENT NO. : 5,322,844
DATED : June 21, 1994
INVENTOR(S) : Julian Aranda, et al.

It is certified that error appears in the above-indentified patent and that said Letters Patent is hereby corrected as shown below:

Column 34, line 16, "methyl]-4-piperazine" should read "methyl]-4-benzylpiperazine".

Column 34, line 18, "sesquixalate" should read "sesquioxalate"

Column 34, line 20 "pyridon" should read "pyridone".

Column 34, line 22 "pyridon" should read "pyridone".

Column 34, line 24 "pyridon" should read "pyridone".

Column 34, line 26 "pyridon" should read "pyridone".

Column 32, line 27, "piperzine" should read "piperazine".

Column 34, line 29, "5-octadecyloxy-4(1H)-pyridon" should read "5-decyloxy-4(1H)-pyridone".

Column 34, line 30, "piperidine" should read "piperazine".

UNITED STATES PATENT AND TRADEMARK OFFICE
CERTIFICATE OF CORRECTION

PATENT NO. : 5,322,844
DATED : June 21, 1994
INVENTOR(S) : Julian Aranda, et al.

It is certified that error appears in the above-indentified patent and that said Letters Patent is hereby corrected as shown below:

```
Column 34, line 32, "5-ocatdecyloxy-" should read
"5-octadecyloxy-".
```

Signed and Sealed this

Twentieth Day of September, 1994

*Attest:*

*Attesting Officer*

BRUCE LEHMAN
*Commissioner of Patents and Trademarks*